United States Patent
Erb et al.

(10) Patent No.: US 10,596,757 B2
(45) Date of Patent: Mar. 24, 2020

(54) THREE DIMENSIONAL MINERALIZATION PRINTER

(71) Applicants: Northeastern University, Boston, MA (US); Colorado School of Mines, Golden, CO (US)

(72) Inventors: Randall Morgan Erb, Newton, MA (US); Melissa Krebs, Englewood, CO (US); Tyler Hall, Boxford, MA (US); Kelli Ann Lynch, Fort Collins, CO (US); Conor Michael Doyle, Sherborn, MA (US); Isabel Welch, Uxbridge, MA (US); Peter Christensen, Ridgefield, CT (US)

(73) Assignees: Northeastern University, Boston, MA (US); Colorado School of Mines, Golden, CO (US)

( * ) Notice: Subject to any disclaimer, the term of this patent is extended or adjusted under 35 U.S.C. 154(b) by 0 days.

(21) Appl. No.: 15/832,562

(22) Filed: Dec. 5, 2017

(65) Prior Publication Data
US 2018/0243980 A1   Aug. 30, 2018

Related U.S. Application Data

(60) Provisional application No. 62/430,800, filed on Dec. 6, 2016.

(51) Int. Cl.
*B29C 64/357* (2017.01)
*B33Y 10/00* (2015.01)
(Continued)

(52) U.S. Cl.
CPC ........ *B29C 64/165* (2017.08); *A61C 13/0019* (2013.01); *B29C 64/106* (2017.08);
(Continued)

(58) Field of Classification Search
None
See application file for complete search history.

(56) References Cited

U.S. PATENT DOCUMENTS 5,370,692 A * 12/1994 Fink ...................... B29C 64/165
                                                          128/898
6,733,503 B2   5/2004 Layrolle et al.
(Continued)

OTHER PUBLICATIONS

Markstedt et al, "3D Bioprinting Human Chondrocytes with Nanocellulose—Alginate Bioink for Cartilage Tissue Engineering Applications", BioMacromolecules, pp. 1489-1496. (Year: 2016).*
(Continued)

*Primary Examiner* — Mary Lynn F Theisen
(74) *Attorney, Agent, or Firm* — Sheridan Ross P.C.

(57) ABSTRACT

Augmented three-dimensional (3D) printing systems and methods for constructing and mineralizing a hydrogel structure with defined geometry are disclosed. One example embodiment is a system for three-dimensional printing and mineralizing a polymer. The system includes a three-dimensional printer unit with a syringe extruder, a fluid delivery system operatively coupled to the three-dimensional printer unit, and a control unit. The control unit is operatively coupled to the three-dimensional printer unit and fluid delivery system, and is configured to (i) cause the three-dimensional printer unit to print a portion of a three-dimensional polymer object, (ii) cause the fluid delivery system to flush the portion of the three-dimensional polymer object with a fluid to mineralize the portion of the three-dimensional polymer object, and (iii) cause the three-dimensional printer unit to print a subsequent portion of the three-dimensional polymer object. Applications of embodiments include manufacturing of tooth, bone, and other biomaterial articles.

21 Claims, 11 Drawing Sheets

(51) Int. Cl.
    B33Y 30/00      (2015.01)
    B29C 64/106     (2017.01)
    B29C 64/393     (2017.01)
    B33Y 50/02      (2015.01)
    B29C 64/165     (2017.01)
    B29C 64/295     (2017.01)
    A61C 13/00      (2006.01)
    B33Y 80/00      (2015.01)
    G05B 19/4097    (2006.01)
    B29C 64/255     (2017.01)
    B29C 71/00      (2006.01)
    B29C 64/209     (2017.01)
    B29C 64/188     (2017.01)

(52) U.S. Cl.
    CPC .......... *B29C 64/188* (2017.08); *B29C 64/209* (2017.08); *B29C 64/255* (2017.08); *B29C 64/295* (2017.08); *B29C 64/357* (2017.08); *B29C 64/393* (2017.08); *B29C 71/0009* (2013.01); *B33Y 10/00* (2014.12); *B33Y 30/00* (2014.12); *B33Y 80/00* (2014.12); *G05B 19/4097* (2013.01); *B29C 2071/0018* (2013.01); *B33Y 50/02* (2014.12)

(56) References Cited

U.S. PATENT DOCUMENTS

| | | | |
|---|---|---|---|
| 7,682,540 B2* | 3/2010 | Boyan | A61L 27/16 264/212 |
| 2004/0236432 A1 | 11/2004 | Hyon et al. | |
| 2005/0082710 A1* | 4/2005 | Oriakhi | A61K 6/0835 264/113 |
| 2006/0134160 A1 | 6/2006 | Troczynski et al. | |
| 2007/0098799 A1 | 5/2007 | Zhang et al. | |
| 2014/0312535 A1* | 10/2014 | Dikovsky | A61C 13/0019 264/401 |
| 2016/0346429 A1 | 12/2016 | Krebs et al. | |
| 2017/0326272 A1 | 11/2017 | Harding et al. | |
| 2018/0171304 A1* | 6/2018 | Beyer | C12M 21/08 |
| 2018/0235739 A1* | 8/2018 | Jahn | A61C 13/0004 |
| 2018/0298215 A1* | 10/2018 | Andersen | C04B 28/006 |

OTHER PUBLICATIONS

"ChronOS® Bone Void Filler," DePuySynthes, 2014, 8 pages.
"HydroSet Injectable Bone Substitute," brochure, Stryker, 2014, 6 pages.
"PRO-DENSE® Graft-Bone Graft Substitute," Wright, 2015, retrieved from https://web.archive.org/web/*/http://www.wright.com/physicians/prodense/product-overview, 2 pages.
Bleek et al., "New developments in polymer-controlled, bioinspired calcium phosphate mineralization from aqueous solution," Acta Biomaterialia, 2013, vol. 9(5), pp. 6283-6321, 2 pages, abstract only.
Dorozhkin et al., "Biological and Medical Significance of Calcium Phosphates," Angewandte Chemie, 2002, vol. 41(17), pp. 3130-3146, 3 pages, abstract only.
Elliott, "Mineral, synthetic and biological carbonate apatites," Structure and Chemistry of the Apatites and Other Calcium Orthophosphates (book), Elsevier, 1994, pp. 191-304, 1 pages, abstract only.
Harding et al., "Controlled and Tunable Biomimetic Apatite Mineralization of Synthetic Hydrogels," Macromolecular Materials and Engineering, 2016, 3 pages, abstract only.
Hassan et al., "Structure and Applications of Poly(vinyl alcohol) Hydrogels Produced by Conventional Crosslinking or by Freezing/Thawing Methods," Advanced Polymer Science, 2000, vol. 153(37), pp. 37-65.
John et al., "A trial to prepare biodegradable collagen-hydroxyapatite composites for bone repair," Journal of Biomaterials Science—Polymer Edition, 2001, vol. 12(6), pp. 689-705, abstract only, 2 pages.
Kumar et al., "Transformation of modified brushite to hydroxyapatite in aqueous solution: effects of potassium substitution," Biomaterials, 1999, vol. 20(15), pp. 1389-1399, 2 pages, abstract only.
Oonishi et al., "Clinical Application of Hydroxyapatite in Orthopedics," Advances in Calcium Phosphate Biomaterials, Chapter 2, 2014, pp. 19-49.
Raynaud et al., "Calcium phosphate apatites with variable Ca/P atomic ratio I. Synthesis, characterisation and thermal stability of powders," Biomaterials, 2002, vol. 23(4), pp. 1065-1072, 1 page, abstract only.
Rezwan et al., "Biodegradable and bioactive porous polymer/inorganic composite scaffolds for bone tissue engineering," Biomaterials, 2006, vol. 27(18), pp. 3413-3431, 1 page, abstract only.
Schweizer et al., "Polymer-Controlled, Bio-Inspired Calcium Phosphate Mineralization from Aqueous Solution," Macromolecular Bioscience, 2007, vol. 7(9-10), pp. 1085-1099, abstract only, 2 pages.
Zadpoor, "Relationship between in vitro apatite-forming ability measured using simulated body fluid and in vivo bioactivity of biomaterials," Materials Science and Engineering: C, 2014, vol. 35, pp. 134-143, abstract only, 2 pages.
Official Action for U.S. Appl. No. 15/170,630 dated Oct. 3, 2017, 9 pages, Restriction Requirement.
Official Action for U.S. Appl. No. 15/170,630 dated Jan. 30, 2018, 12 pages.
Official Action for U.S. Appl. No. 15/170,630 dated Jun. 11, 2018, 15 pages.
Official Action for U.S. Appl. No. 15/170,630 dated Oct. 22, 2018, 16 pages.
Official Action for U.S. Appl. No. 15/595,310, dated Jun. 11, 2018, 7 pages. Restriction Requirement.
Official Action for U.S. Appl. No. 15/595,310, dated Dec. 13, 2018, 10 pages.

* cited by examiner

| | |
|---|---|
| Pause before mineralizing (ms) | 2000 |
| Head park X (mm) | 100 |
| Head park Y (mm) | 100 |
| Z soft limit (mm) | 104.25 |

Retraction

| | |
|---|---|
| Speed (mm/s) | 30 |
| Distance (mm) | Speed at which the filame retraction speed works be speed can lead to filamen |

Quality

| | |
|---|---|
| Initial layer thickness (mm) | 0.3 |
| Initial layer line width (%) | 100 |
| Cut off object bottom (mm) | 0.0 |
| Dual extrusion overlap (mm) | 0.15 |

Speed

| | |
|---|---|
| Travel speed (mm/s) | 35 |
| Bottom layer speed (mm/s) | 35 |
| Infill speed (mm/s) | 0.0 |
| Top/bottom speed (mm/s) | 0.0 |
| Outer shell speed (mm/s) | 0.0 |
| Inner shell speed (mm/s) | 0.0 |

Cool

| | |
|---|---|
| Minimal layer time (sec) | 5 |
| Enable cooling fan | |

Quality

| | |
|---|---|
| Layer height (mm) | 0.2 |
| Shell thickness (mm) | 5 |
| Enable retraction | |

Fill

| | |
|---|---|
| Bottom/Top thickness (mm) | 0.3 |
| Fill Density (%) | 100 |

Speed and Temperature

| | |
|---|---|
| Print speed (mm/s) | 1 |
| Printing temperature (C) | 60 |

Support

| | |
|---|---|
| Support type | None |
| Platform adhesion type | None |

Filament

| | |
|---|---|
| Diameter (mm) | 6 |
| Flow (%) | 7 |

Machine

| | |
|---|---|
| Nozzle size (mm) | .8 |

FIG. 7

THREE DIMENSIONAL MINERALIZATION PRINTER

RELATED APPLICATION

This application claims the benefit of U.S. Provisional Application No. 62/430,800, filed on Dec. 6, 2016. The entire teachings of the above application are incorporated herein by reference.

BACKGROUND

The present disclosure is concerned with three-dimensional (3D) printing of polymers. Collagen is an example of a biological hydrogel polymer and is an important component of bones, teeth, and other tissues, for example. A two-stage chemical process can be used to transform collagen into hardened tooth mineral by cyclic immersion in calcium and phosphate salt solutions, followed by maturation in a buffered solution at constant temperature and pH. While this technology can create such biomaterials, it is not capable of forming them into a defined structure, like a human tooth, for example. Additionally, the process is time-consuming, laborious, and to date has only been performed on amorphous collagen samples.

SUMMARY

Disclosed herein are augmented 3D printing systems and methods for constructing and mineralizing a hydrogel structure with defined geometry that can be subsequently matured into a hardened mineral (e.g., tooth dentin or enamel). One example embodiment is a system for three-dimensional printing and mineralizing a polymer. The system includes a three-dimensional printer unit with a syringe extruder, a fluid delivery system operatively coupled to the three-dimensional printer unit, and a control unit. The control unit is operatively coupled to the three-dimensional printer unit and fluid delivery system, and is configured to (i) cause the three-dimensional printer unit to print a portion of a three-dimensional polymer object, (ii) cause the fluid delivery system to flush the portion of the three-dimensional polymer object with a fluid to mineralize the portion of the three-dimensional polymer object, and (iii) cause the three-dimensional printer unit to print a subsequent portion of the three-dimensional polymer object.

In many embodiments, the fluid delivery system can include a chamber in which the three-dimensional polymer object is printed, at least one fluid reservoir, and at least one pump in fluid communication with the chamber and the fluid reservoir to transfer fluid from the fluid reservoir to the chamber. The chamber can include a fluid level sensor in communication with the control unit and that prevents over-filling of the chamber. The chamber can include a drain to remove fluid from the chamber. In such embodiments, the fluid delivery system can include at least one recycling reservoir in fluid communication with the drain to receive fluid from the chamber for reuse.

In some embodiments, the fluid delivery system can include (i) two main fluid reservoirs, (ii) two main pumps in communication with the control unit, and in fluid communication with the chamber and the respective fluid reservoirs to transfer fluid from the fluid reservoirs to the chamber, (iii) two recycling reservoirs, and (iv) two recycling pumps in communication with the control unit, and in fluid communication with the chamber and the respective recycling reservoirs to transfer fluid from the chamber to the recycling reservoirs and from the recycling reservoirs to the chamber. In such embodiments, a first of the two main fluid reservoirs can contain a first salt solution with a given cation, and a second of the two main fluid reservoirs can contain a second salt solution with a given anion. A first of the two recycling reservoirs can contain at least a portion of the first salt solution after being used to flush at least a portion of a three-dimensional polymer object, and a second of the two recycling reservoirs can contain at least a portion of the second salt solution after being used to flush at least a portion of a three-dimensional polymer object.

In some embodiments, the syringe extruder can include an insulated extended copper-lined tip to maintain a heated polymer within a certain temperature range as the heated polymer passes through the extended tip. The polymer extruded by the syringe extruder may be charged. In some embodiments, the control unit can configured to respond to custom commands inserted into a set of three-dimensional printing commands used by the three-dimensional printer unit. In such embodiments, the custom commands can include commands that cause the three-dimensional printer unit to pause and resume printing.

Another example embodiment is method for three-dimensional printing and mineralizing a polymer. The method includes printing a portion of a three-dimensional polymer object, flushing the portion of the three-dimensional polymer object with a fluid to mineralize the portion of the three-dimensional polymer object, and printing a subsequent portion of the three-dimensional polymer object. The three-dimensional polymer object can be matured by immersing the three-dimensional polymer object in a buffer solution. In some embodiments, flushing the portion of a three-dimensional polymer object with fluid can include (i) transferring a first fluid from a first main reservoir to a chamber in which the three-dimensional polymer object is printed, (ii) transferring the first fluid from the chamber to a first recycling reservoir, (iii) transferring a second fluid from a second main reservoir to the chamber, and (iv) transferring the second fluid from the chamber to a second recycling reservoir.

Another example embodiment is a method for three-dimensional printing and mineralizing a polymer. The method includes generating a set of three-dimensional printing commands to be used by a three-dimensional printer unit to print a three-dimensional polymer object, inserting custom commands into the set of three-dimensional printing commands, the custom commands including commands that cause the three-dimensional printer unit to pause and resume printing, and according to the set of three-dimensional printing commands with the custom commands, (i) printing a portion of a three-dimensional polymer object, (ii) flushing the portion of the three-dimensional polymer object with a fluid to mineralize the portion of the three-dimensional polymer object, and (iii) printing a subsequent portion of the three-dimensional polymer object. In many embodiments, the set of three-dimensional printing commands with the custom commands can cause the three-dimensional printer unit to pause printing before flushing the portion of the three-dimensional polymer object with the fluid, and resume printing after flushing the portion of the three-dimensional polymer object with the fluid. In many embodiments, the set of three-dimensional printing commands causes activation and deactivation of pumps and valves to flush the portion of the three-dimensional polymer object with the fluid.

BRIEF DESCRIPTION OF THE DRAWINGS

The foregoing will be apparent from the following more particular description of example embodiments, as illus

FIG. 7 illustrates example three-dimensional printing software program parameters for syringe extrusion of a polymer, according to an example embodiment.

DETAILED DESCRIPTION

A description of example embodiments follows.

One example embodiment is an augmented three-dimensional (3D) printing system capable of extruding and mineralizing hydrogel into, for example, a calcium phosphate mineral. Various aspects of the system include hydrogel extrusion, fluid delivery, electronics, and software controls. A commercially-available 3D direct-write printer can be modified with a heated syringe paste extruder outfitted with a custom extrusion needle, for example, and a fluid delivery system that can include, for example, multiple peristaltic pumps and dedicated reservoirs for different salt solutions. Custom circuitry, firmware modifications, and a software plugin can be used to integrate seamlessly the printing and mineralization processes. The system can operate autonomously once a desired 3D geometry is imported, salt solutions are supplied, and parameter values are set.

For some particular applications (e.g., applications relating to dental implants), the commercially-available 3D printer should be capable of extruding a hydrogel structure with geometric fidelity to CAD with 200 μm resolution (layer height), and should be able to print a ½"×⅜"×⅜" structure. The fluid delivery system should be able to control at least three fluids: a salt solution with a given cation (e.g., calcium nitrate), an salt solution with a given anion (e.g., potassium phosphate), and a fluid (e.g., water) rinse. The salt solutions should remain segregated to minimize undesired mineralization. In many embodiments, the printed polymer can be charged (positively, negatively, or regions of both), resulting in a stronger mineralization. Custom controls for the process can be used to stop the printer at variable intervals to perform the mineralization sequence autonomously. The controls can interface with the printer to avoid collision between the modified extrusion head and print stage hardware (chamber). The user may be able to change parameters that affect the mineralization process, such as how often to mineralize, how many cycles to perform, and how long to expose the hydrogel to each solution.

Figure 1:
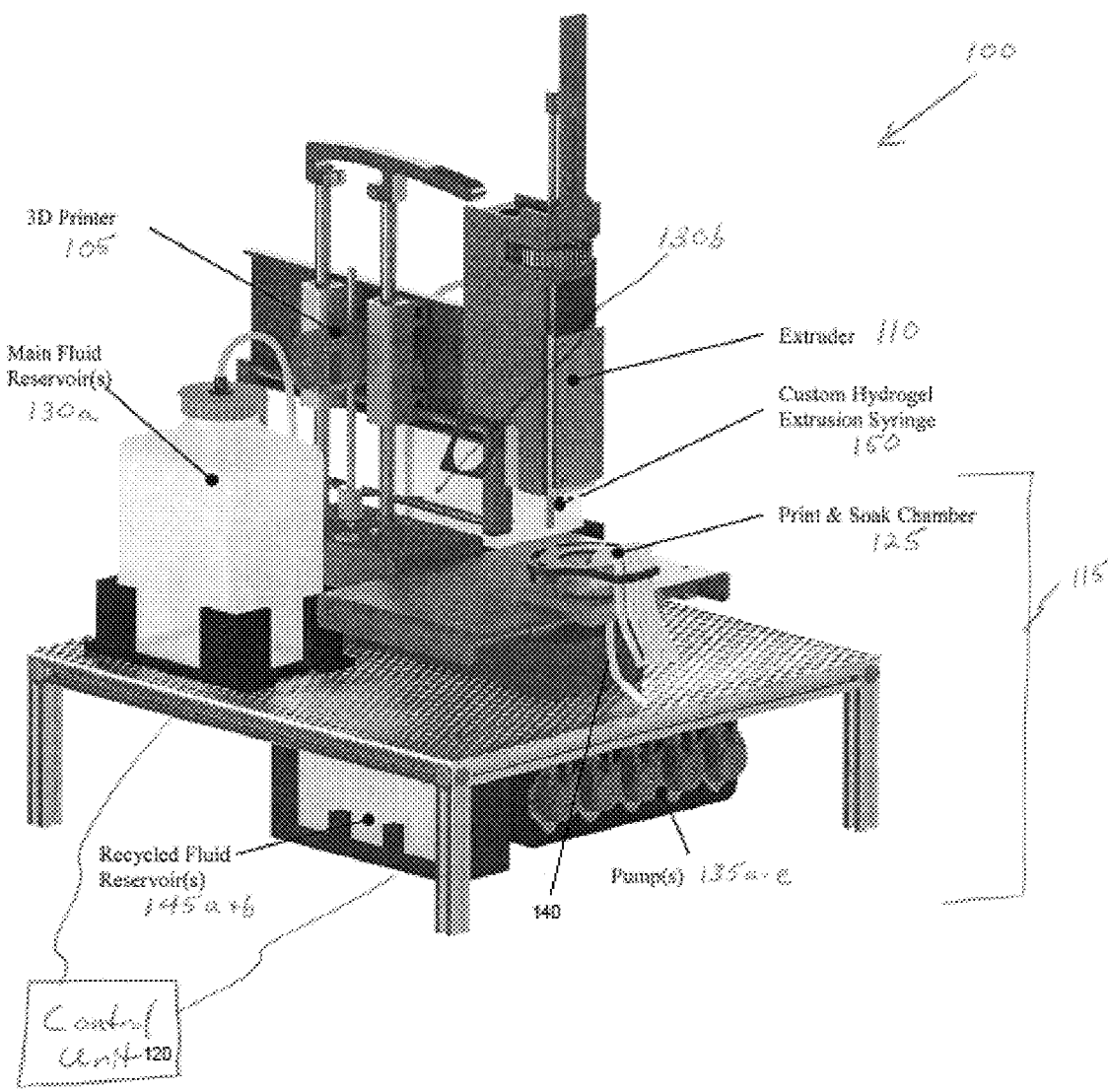
- FIG. 1 is a schematic diagram illustrating a three-dimensional mineralization printer system, according to an example embodiment.

FIG. 1 is a schematic diagram illustrating an example three-dimensional mineralization printer system 100, according to an example embodiment. The system 100 includes a three-dimensional printer unit 105 with a syringe extruder 110, a fluid delivery system 115 operatively coupled to the three-dimensional printer unit 105, and a control unit 120. The syringe extruder 110 of the example system 100 includes an insulated extended copper-lined tip to maintain a heated polymer within a certain temperature range as the heated polymer passes through the extended tip. The control unit 120 is operatively coupled to the three-dimensional printer unit 105 and fluid delivery system 115. The control unit 120 can be integrated with the three-dimensional printer unit 105 or the fluid delivery system 115, or may be a separate component that is in communication with the three-dimensional printer unit 105 and the fluid delivery system 115 by wired or wireless connections. The control unit 120 is configured to (i) cause the three-dimensional printer unit 105 to print a portion of a three-dimensional polymer object, (ii) cause the fluid delivery system 115 to flush the portion of the three-dimensional polymer object with a fluid to mineralize the portion of the three-dimensional polymer object, and (iii) cause the three-dimensional printer unit 105 to print a subsequent portion of the three-dimensional polymer object.

In the example system 100, the fluid delivery system 115 can include a chamber 125 in which the three-dimensional polymer object is printed, at least one fluid reservoir 130, and at least one pump 135 in fluid communication with the chamber and the fluid reservoir to transfer fluid from the fluid reservoir 130 to the chamber 125. The chamber 125 can include a fluid level sensor (not shown) in communication with the control unit 120 and that prevents over-filling of the chamber 125. The chamber 125 can include a drain 140 to remove fluid from the chamber 125. In the example system 100, the fluid delivery system 115 includes at least one recycling reservoir 145 in fluid communication with the drain 140 to receive fluid from the chamber 125 for reuse. In the example system 100, the fluid delivery system 115 includes two main fluid reservoirs 130a, 130b, two main pumps 135a, 135b in communication with the control unit 120 and in fluid communication with the chamber 125 and the respective fluid reservoirs 130a, 130b to transfer fluid from the fluid reservoirs 130a, 130b to the chamber 125. The fluid delivery system 115 also includes two recycling reservoirs 145a, 145b, and two recycling pumps 135c, 135d in communication with the control unit 120 and in fluid communication with the chamber 125 and the respective recycling reservoirs 145a, 145b to transfer fluid from the chamber 125 to the recycling reservoirs 145a, 145b and from the recycling reservoirs 145a, 145b to the chamber 125. Pump 135e can be used to transfer fluid from the drain of the chamber 125 to a waste location (e.g., a waste reservoir or drain).

Figure 2:
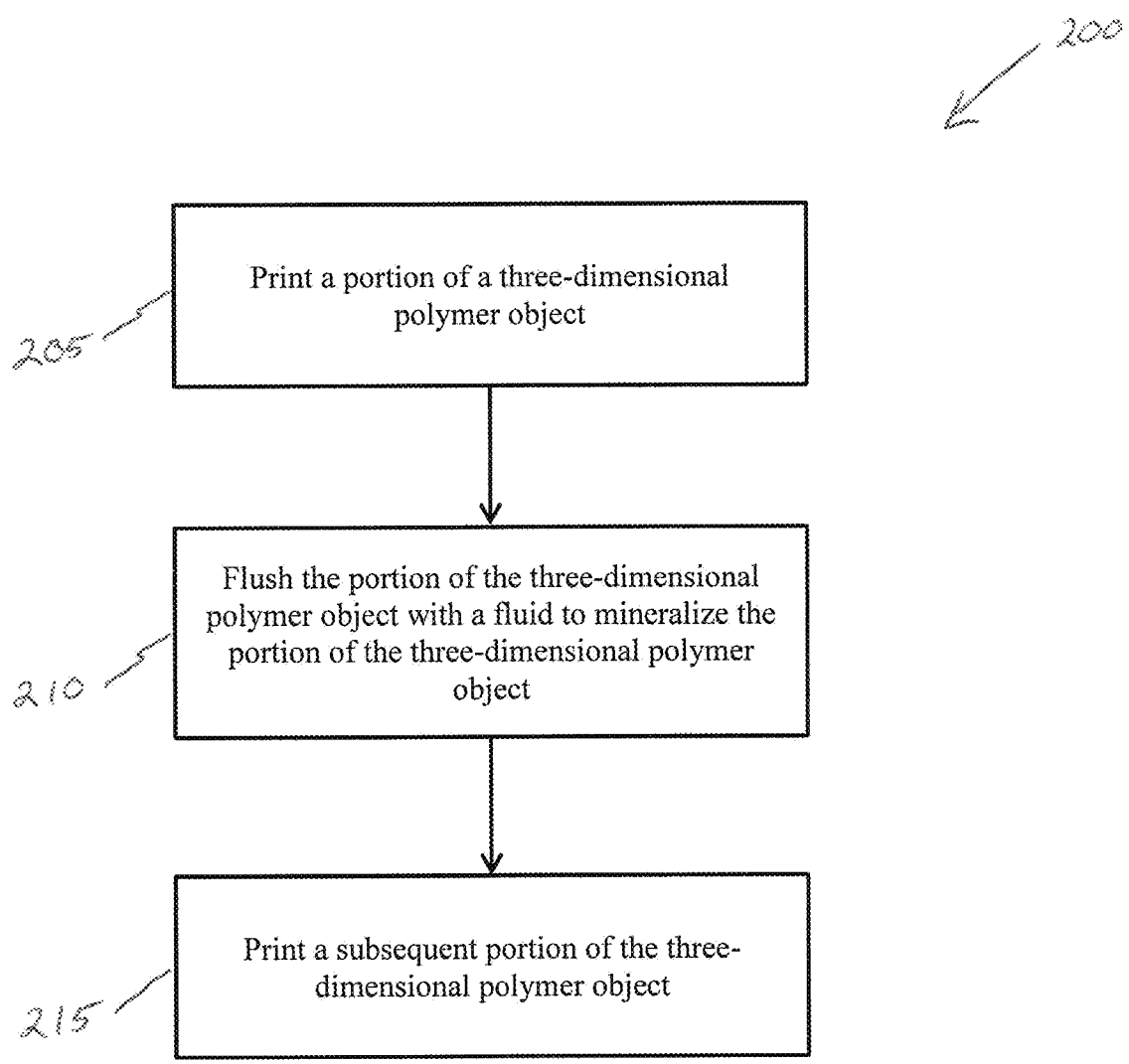
FIG. 2 is a flow diagram illustrating a method for printing and mineralizing a polymer, according to an example embodiment.

FIG. 2 is a flow diagram illustrating a method 200 for printing and mineralizing a polymer, according to an example embodiment. The example method 200 includes printing 205 a portion of a three-dimensional polymer object, flushing 210 the portion of the three-dimensional polymer object with a fluid to mineralize the portion of the three-dimensional polymer object, and printing 215 a subsequent portion of the three-dimensional polymer object.

Figure 3:
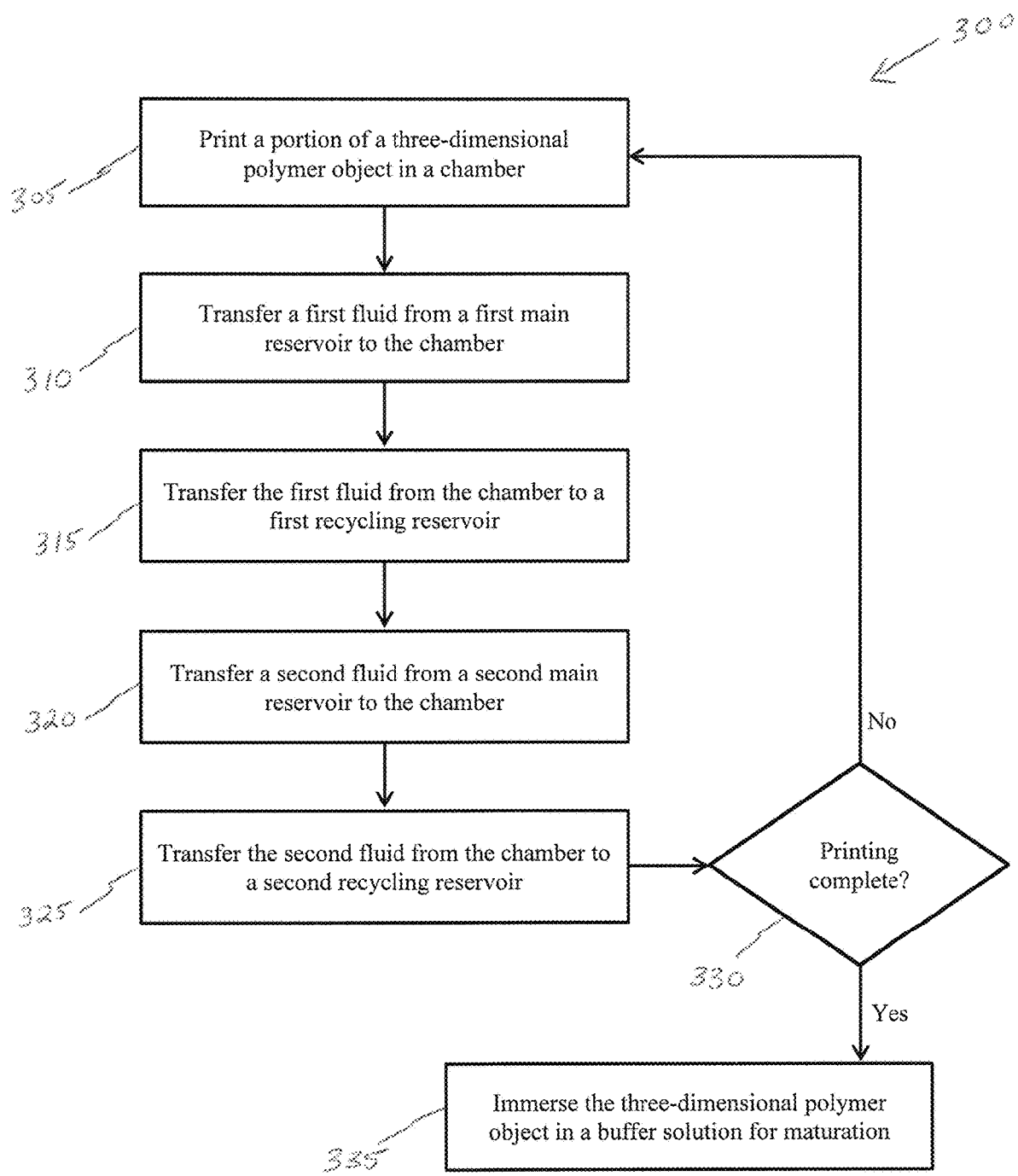
FIG. 3 is a flow diagram illustrating a method for printing and mineralizing a polymer, according to an example embodiment.

FIG. 3 is a flow diagram illustrating a method 300 for printing and mineralizing a polymer, according to an example embodiment. The example method 300 includes printing 305 a portion of a three-dimensional polymer object in a chamber, transferring 310 a first fluid from a first main reservoir to the chamber, transferring 315 the first fluid from the chamber to a first recycling reservoir, transferring 320 a second fluid from a second main reservoir to the chamber, and transferring 325 the second fluid from the chamber to a second recycling reservoir. If the printing process is not yet completed 330, the process can continue by printing 305 a subsequent portion of the three-dimensional polymer object. If the printing process has completed 330, then the three-dimensional polymer object can be matured by immersing 335 the three-dimensional polymer object in a buffer solution.

To aide in describing the details of particular embodiments of the disclosed systems and methods, the following is a general explanation of the composition and formation of human teeth. It should be understood that while one example application for the systems and methods disclosed herein is the printing and mineralization of dental or other biomineral implants, the systems and methods can similarly be applied to other technological areas.

Teeth have five main components: enamel, dentin, dentin enamel junction (DEJ), pulp, and cementum. Enamel is the hardest component in teeth and the most mineralized material in the human body, making it wear resistant and ideal for mastication. It is composed of approximately 95% carbonated apatite, 1% organic matter, and 4-5% water. The carbonated apatite is hydroxyapatite, which is a crystalline calcium phosphate that forms hexagonal-prism rods 3-5 μm in diameter. Dentin, the main body of teeth, is 70% hydroxyapatite that forms crystalline phosphoric apatite, 20% organic material, and 10% water. Greater elasticity and decreased hardness allows for dentin to absorb forces associated with chewing. The dentin-enamel junction (DEJ) lies between enamel and dentin. While most enamel is highly mineralized and lacks collagen, VII collagen is in the enamel matrix near the DEJ. VII collagen is a protein found in skin that helps anchor epidermis and dermis layers together. VII collagen fibrils near the DEJ may increase fracture resistance and help bond enamel to dentin. Pulp is the soft core of teeth that connects to blood vessels and nerves. Cementum is the connective tissue surrounding the roots that connects the tooth to the gums and jaw.

Current tooth replacement technologies include dental implants that replace damaged or missing teeth, and that providing patients with a structural and aesthetic analog. Most implants are anchored into the jaw with a tapped post. The post implanted into the jaw can be made from either zirconia ceramic or, more commonly, titanium. An abutment is mounted onto the post, allowing different prosthetics to be attached.

Formation of Collagen and Gelatin

An aspect of embodiments of the disclosed systems and methods is successful hydrogel extrusion. A hydrogel is a polymeric network that is saturated with water. Collagen and gelatin are both hydrophilic biopolymers that swell and form hydrogels when exposed to water. The presence of water in the gel allows for the diffusion of calcium and phosphate ions.

Collagen is a structural biological polymer that is integral to the creation of tendons, skin, blood vessels, and more. It is composed of three procollagen chains arranged in a triple-helix structure. These triple helices can arrange multiple ways to produce different types of collagen. Type I collagen, or fibrillar collagen, forms bone and teeth. The fibrillar structure forms when collagen helices align slightly offset from one another, resulting in gaps and overlaps.

Type VII collagen is not found in dentin or enamel, but rather the junction between the two (the DEJ) in human teeth. This type of collagen contains a region of disordered amino acids which serve as bonding sites. This may explain type VII collagen's role in binding dermal tissue to the basement membrane in the human body. Its function in the skin suggests it may have an adhesive effect between dentin and enamel.

Hydrolysis of collagen produces gelatin, a water soluble protein. This process destroys the tertiary structure of the collagen by breaking covalent and hydrogen bonds among the fibrils. There are many types of gelatin, differentiated by the degree of cross-linking in the parent collagen, and the temperature and pH of hydrolysis. During cross-linking, molecules with reactive ends form covalent bonds with functional groups on other molecules, which is the final step in the formation of fibrillar collagen. The hydrolysis of collagen reverses this process to produce gelatin.

Gelatin quality is classified by gel strength and thermostability. These properties are determined by amino acid composition and molecular weight distribution. Gelatin is much less expensive and more widely available than collagen. It is important to note the different thermal behavior of collagen and gelatin to ensure that the printer is adapted to both materials. Gelatin melts at 46.3° C. and collagen, depending on its processing, melts at 37.5° C. The extruders used in many 3D printing systems are capable of heating at or above this temperature.

Heating collagen or gelatin rapidly unfolds its triple helix structure, resulting in a lower viscosity fluid. According to some embodiments of the systems and methods disclosed herein, gelatin is heated to 60° C., above gelatin's melting point but below its denaturing temperature. After cooling, the triple helix refolds in a process called gelation. In the printer, gelation at room temperature allows print geometry to be controlled.

Current 3D Printing Technology

Direct-writing is a category of 3D printing in which material is deposited, dispensed, or processed in a pattern to generate a three dimensional structure. Direct-write printers can be categorized by material delivery mechanism: droplet, energy beam, flow, or tip-based. In droplet printing, liquid is deposited in a continuous stream or individual droplets and solidified by solvent evaporation or temperature control. Energy beam direct writing uses a laser or focused ion beam (FIB) to drive the deposition of the build material, forming a three dimensional structure. Flow printers use positive mechanical pressure from a positive displacement pump, syringe extrusion, or air pressure to deposit material onto the print site. Tip printers are used for nanomanufacturing through either dip-pin lithography or micro-pipetting.

Energy beam systems produce high resolution prints at moderate speed and vertical structure quality, but can be very costly. In contrast, droplet printing is very low cost, but intended to create low vertical structure and would not generate the desired print height. Extrusion based printers come at moderate cost, with moderate resolution and the ability to create vertical structure. In some embodiments of the disclosed systems and methods, a printer issued that prints at a high resolution of 200 μm and that is capable of creating a ⅜ inch or taller vertical structure.

An initial step in producing a fully matured biomineral structure is the creation of a scaffold on which the minerals can develop. Collagen hydrogels are a good scaffold choice because they are a major component of biological tissues, suitable to a variety of applications, and easily acquired.

In an unaltered state, hydrogels are semi-solid and must be liquefied for extrusion in a 3D printer. A common liquefaction technique involves dispersing collagen in solutions of acetic or phosphoric acid and subsequently solidifying the printed structure in a freeze-dryer. Collagen can also be melted at around 40-60° C. and cooled to solidify after extrusion. The latter process may be used by many embodiments of the disclosed systems and methods.

Mineralization of Hydrogel to Dicalcium Phosphate Dihydrate (DCPD)

Once the hydrogel is extruded and gelled, the next stage is mineralization: the deposition of a calcium phosphate mineral within the collagen scaffold. During this process, the hydrogel can be exposed to alternating solutions of calcium nitrate ($CaNO_3$)—a source of calcium ions—and potassium phosphate dibasic ($K_2HPO_4$)—a source of phosphate ions. Calcium and phosphate ions bind to active sites within the hydrogel matrix and form dicalcium phosphate dihydrate (DCPD, $CaHPO_4.2H_2O$). The baths can last for approximately three minutes each, with DI water rinses in between. This process was tested with a range of 1-50 cycle repetitions, and observed little further change in the structure after 20 cycles.

The kinetics of the mineralization process are controlled primarily by diffusion of the ions into the hydrogel. Diffusion is a function of volume, surface area, porosity, and solute size among other variables. One challenge in particular is the tendency of the mineralizing ions (e.g., $Ca^+$, $PO_4^{2-}$) to bond to the surface of the hydrogel and limit further diffusion into the body. 3D printing enables a high level of control over these geometric parameters, allowing researchers to tune the precise shape and volume of hydrogel to be mineralized and to incorporate macro-scale porosity to facilitate diffusion.

Maturation of DCPD

Following mineralization, the crystal structure of the DCPD-hydrogel is matured, or transformed, into a different mineral. The structure can be immersed in a TRIS (trishydroxymethylaminomethane) buffer solution for three to five days maintained, for example, at physiologic temperature (37° C.) and pH (7.4). During this time, the DCPD is hydrolyzed into mature apatite, a common biological mineral composed of calcium and phosphate. Apatite minerals are a primary component of bone and teeth. The character of the mature apatite can be tuned by changing the ions present in the solution during the maturation process. For example, fluoride ($F^-$, as NaF), will yield an enamel analogue, and carbonate ($CO_3^{2-}$, as a component of simulated body fluid) will yield a dentin analogue. It was found that calcium phosphate samples can be matured in a 4° C. refrigerator for 3-5 days to obtain full maturation of crystals.

Unlike the mineralization process, which is diffusion-limited, the three to five days required for maturation owes to the time required for hydrolysis and the transformation from DCPD to apatite. Temperature and pH can influence this process to a limited degree. This means that the time requirement for maturation is relatively fixed. Maturation can occur outside of the 3D printing system as a separate post-process.

Experimentation with Hydrogel

Gelatin Mineralization Experiment

As an experiment, a gummy bear served as a gelatin structure. Calcium nitrate ($CaNO_3$) and dipotassium phosphate ($K_2HPO_4$) solutions were prepared according to the following calculations:

0.25M Calcium nitrate:
Solute Molar Mass: 164.09 g/mol
Desired Concentration: 41.02 g of solute/L $H_2O$
Prepared for Experiment: 125 mL, 5.127 g of solute (pH=6)
0.25M Dipotassium phosphate:
Solute Molar Mass: 174.18 g/mol
Desired Concentration: 43.545 g solute/L $H_2O$
Prepared for Experiment: 125 mL, 5.443 g of solute (pH=7.5)

Prior to mineralization, the gummy bear was soaked in DI water for approximately two hours to saturate the hydrogel. The gummy bear was then placed into the $CaNO_3$ solution for three minutes. Afterwards it was rinsed with DI water and transferred to the $K_2HPO_4$ solution for three minutes. The gummy bear was rinsed in DI water and photographed before the cycle was repeated. The cycle of $CaNO_3 \rightarrow DI \rightarrow K_2HPO_4 \rightarrow DI$ was repeated ten times.

During the first cycle, a white layer formed on the surface soon after the gummy bear was placed into the $K_2HPO_4$ solution. With each additional cycle, the mineralized layer appeared to thicken. Transferring the gummy bear between solutions often resulted in small chunks of the mineralized layer flaking off. However, after additional cycles, a mineralized layer reformed in these areas.

This test proved that surface mineralization on a gelatin structure is possible. Additionally, this test showed that mineralized layers can grow layer by layer, forming a mineralized crystal structure. The process did reveal the delicate state of the mineralized layers, which broke off easily when the gummy bear was being transferred. However, the breaking of the mineralized layers is less problematic within a 3D printer because the collagen structure can remain stationary on the bed throughout the printing and mineralization processes. 3D printing can allow for layer-by-layer mineralization. If the print's layer height is equal to the depth of mineral deposition, a uniformly mineralized structure can be achieved.

Gelatin Maturation Experiment

A test of the maturation process was performed. The goal of the experiment was to convert DCPD, the product of mineralization, to apatite. Porcine skin gelatin was prepared by mixing 20 wt % water with 80 wt % gelatin and stirring at 60° C. overnight. The liquid gelatin was cast in molds and hydrated in DI water for one hour to form a hydrogel. The gelatin then underwent the mineralization procedure described above.

Following mineralization, 1.514 g of TRIS (100 mM) was mixed with DI water and hydrochloric acid to form a solution. A pH meter monitored solution pH as DI water and 0.1M hydrochloric acid (HCl) were added to the TRIS. First, 60 ml of DI water was added, then HCl was added in small increments until pH reached 7.4. Once at appropriate pH, additional DI water was added until the solution reached 125 ml. The mineralized gelatin samples were placed in the TRIS buffer and left in an incubator at 37° C. for three days. X-ray diffraction was performed on the samples to confirm apatite formation.

Gelatin Viscosity Test

Viscosity is an important material property for extrusion. A sphere drop test was used to determine the viscosity of the hydrogel build material—porcine gelatin. By dropping a sphere with a known size and density, the viscosity of the fluid is calculated using Equation 1.

$$\mu = \frac{1}{v} * \left( \frac{d^2 * (\rho_s - \rho_F) * g}{18} \right) \quad \text{Equation 1}$$

For the test, glycerol was tested with the gelatin for standardizing. 9 ml of each material was put into a graduated cylinder with the glycerol at 21° C. and the gelatin held at 70° C. A stainless steel sphere with a diameter of 1 mm was dropped and timed for a travel of 25 mm. The process was repeated five times for each material. The experimental viscosity of the glycerol was 1.526 Pa·s, with an expected viscosity of 1.115 Pa·s. The difference in glycerol viscosity was used to calculate a correction factor to increase the accuracy of the gelatin viscosity measurement resulting in a viscosity of 0.148 Pa·s.

Gelatin Melting Point Test

Heating gelatin is necessary to liquefy the material for proper extrusion. To design a sufficiently heated extruder tip, it was necessary to determine the specific melting temperature of the gelatin. A melting test was conducted on a small sample of gelatin. By applying constant power, the temperature of the material continues to rise until it reaches the melting point, where it levels off until the sample melts completely, when the temperature continues to rise again. The melting temperature was found to be 46.3° C. Based on this value, the main body of the 3D printer extruder can be held at 60° C., with a tip temperature ranging from 45-50° C.

System Design

An example three-dimensional mineralization printer system can include two subsystems: a 3D printer to print a polymer hydrogel part, and a fluid delivery system to expose the printed part to the chemical solutions for mineralization. The ability for the 3D printer to produce a small layer thickness for the printed part is desired to produce high quality prints and to achieve mineralization throughout the printed body.

3D Printer Subsystem

Based on constraints associated with extruding gelatin, a direct-write 3D printer is suitable. This additive manufacturing method is also known as fused deposition modeling (FDM). An off-the-shelf FDM printer can be modified to extruding gelatin. Such off-the-shelf FDM printers include filament extruders, filament extruders with available syringe extruders, and syringe extruders designed for gels. Most FDM printers extrude by forcing a rigid plastic filament (commonly polylactic acid, PLA) though a heated extrusion tip with a geared stepper motor. This method of extrusion does not work well for hydrogels because they are soft and unable to form a rigid filament. Instead, the gelatin should be heated and extruded using positive pressure. The mechanical motion of the 3D printer print stages fall into three categories: a stationary bed, a bed that moves in two horizontal directions while the head moves vertically, and a bed that moves in one horizontal direction with head moving horizontally and vertically. Considering these 3D printer attributes, a Printrbot Simple™ 3D printer, for example, can be used as the 3D printer in embodiments of the disclosed systems.

Fluid System

Figure 4A:
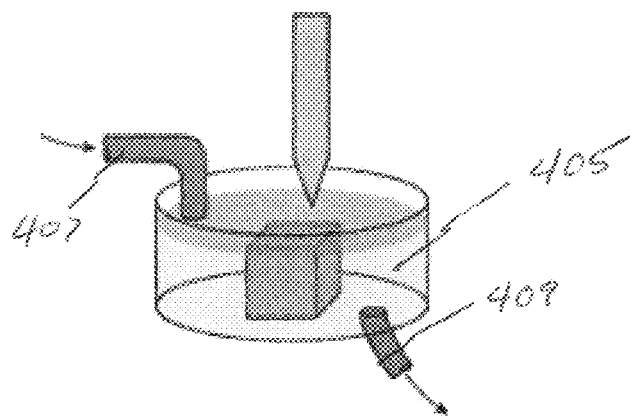
FIGS. 4A-C are schematic diagrams illustrating example designs for integrating chemical solutions with a 3D printer, according to example embodiments.
Figure 4B:
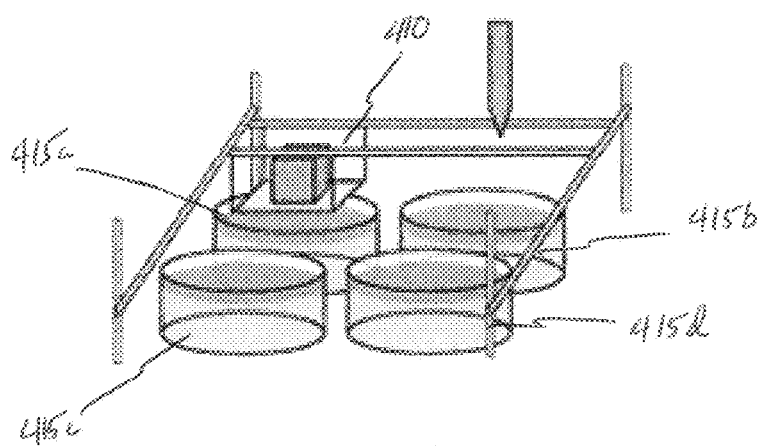
Figure 4C:
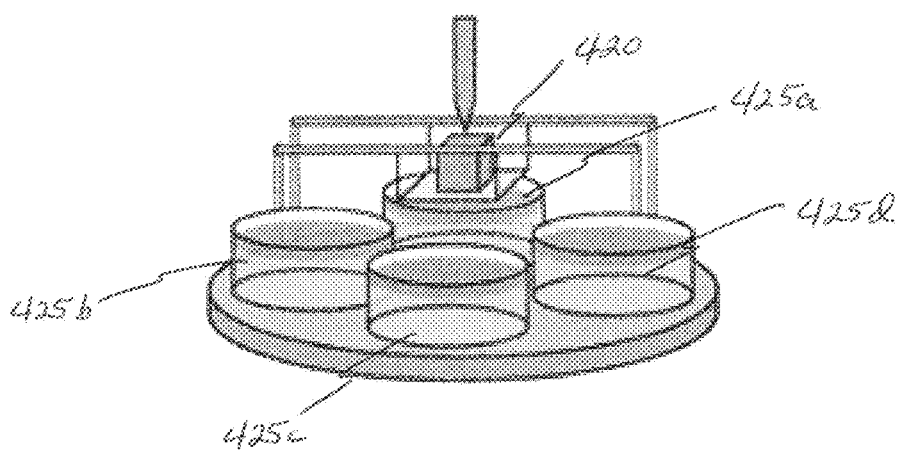

FIGS. 4A-C illustrate three example designs for integrating one or more chemical solution baths with a 3D printer. FIG. 4A illustrates a print stage 405 that serves as a fluid reservoir. FIG. 4B illustrates a moving stage 410 that immerses a printed part in multiple fluid baths 415a-d. FIG. 4C illustrates a stage 420 that moves vertically with multiple fluid baths 425a-d that move as needed.

FIG. 4A illustrates a subsystem with a single chamber 405 for both printing and fluid washing. Inflow tubing 407 delivers mineralization fluids and the fluids exit through an outflow drain 409. This design can use automated pumps and/or valves to deliver fluids to the stage 405. Since the fluids must be drained after each soak period, this design results in greater fluid waste than the designs illustrated in FIG. 4B or 4C. Recycling the fluids back to reservoirs between steps can reduce this waste. The main appeal of the design illustrated in FIG. 4A is that it does not require mechanical motion of the printing stage 405.

In FIG. 4B, a print stage 410 with three axes of motion moves to immerse a printed part into one of several stationary solution reservoirs 415a-d. The benefits of this design are the stationary baths 415a-d, fewer moving parts, and a single solution per reservoir arrangement. However, the stage and part need to home to the exact point where the print head left off after each dipping cycle, potentially causing lower print quality or reliability.

FIG. 4C shows a design in which fluid reservoirs 425a-d rotate or otherwise move underneath the printing assembly 420. The stage 420 then lowers to dip a printed part into each fluid. The stage 420 does not move in the X- or Y-direction during a soak cycle, reducing mechanical complexity and improving reliability. However, the design involves more moving parts than the designs illustrated in FIG. 4A or 4B. The additional motion may also complicate draining or refilling the baths 425a-d.

Example Design and Selection

The design illustrated in FIG. 4A, in which a single bath 405 is cyclically filled with and drained of fluid, can be used in many embodiments. As described above, the mineralization process requires repeated cyclical exposure to three different fluids: 0.25M calcium nitrate, rinse water, and 0.25M potassium phosphate. As the design illustrated in FIG. 4A uses a single bath for all three, the fluids must be drained between cycles and either stored or discarded. Discarding the fluid would require large reservoirs of each solution, and would waste fluid that could be reused. Storing the fluid would require a more complicated system capable of recycling the fluids.

Connecting the printer to a water supply would eliminate the need for a rinse water reservoir and the components to deliver rinse water to the stage. Requiring a water connection for some embodiment is reasonable for a device of this nature. Removing the constraint on the amount of water available can also allow for a more thorough rinse to help minimize cross-contamination between solutions. The solutions can drain into a separate container for safe disposal. In some embodiments, ice may be added to the rinse water to keep the chamber cool during the printing and mineralization process. Keeping the chamber cool helps to stabilize the printed polymers. Further, DI water can be sprayed into the container to aide in rinsing. A pump can be added to the rinse water line to jet water into the tray to provide better rinsing.

An additional advantage of connecting to a water supply is to use the water to dilute salt solutions at much higher concentration than the 0.25M called for in mineralization. This can make it feasible to use fresh fluid for each cycle (no recycling) with reasonably sized reservoirs. Doing so would also simplify the plumbing, but require a mixing system to automatically and precisely dilute the solutions.

Appendix A, below, presents an analysis of the quantities of solution required for fluid systems with recycling, no recycling, and diluting. Based on a 20 mL bath volume, a total print height of 8 mm, 100 μm layer height, and 10 cycles per layer (for a total of 800 cycles), a system without recycling would require 16 liter reservoirs. Supplying fresh solution only after every 10 cycles reduces the required volume to 1.6 liters. Using water to dilute a reservoir of saturated solution would still require reservoir volumes around 0.75 liters, due to the maximum solubility limit of the mineralizing salts in water. Relative to a non-recycling, non-diluting system, diluting reduces only the reservoir volume—not the total required salt. Both methods require around 650 g of each salt under the estimated conditions described above.

Recycling the fluid is also an option. Connecting to a water supply can eliminate the need for a rinse water reservoir and enables more thorough rinsing between cycles. Two different approaches for recycling fluids include recirculating fluid back into the main reservoir for that solution, or into a small separate recycle reservoir. Using a separate reservoir for recycling would add further complexity to the fluid system, but storing used fluids back in the main reservoir could lead to contamination.

Figure 5A:
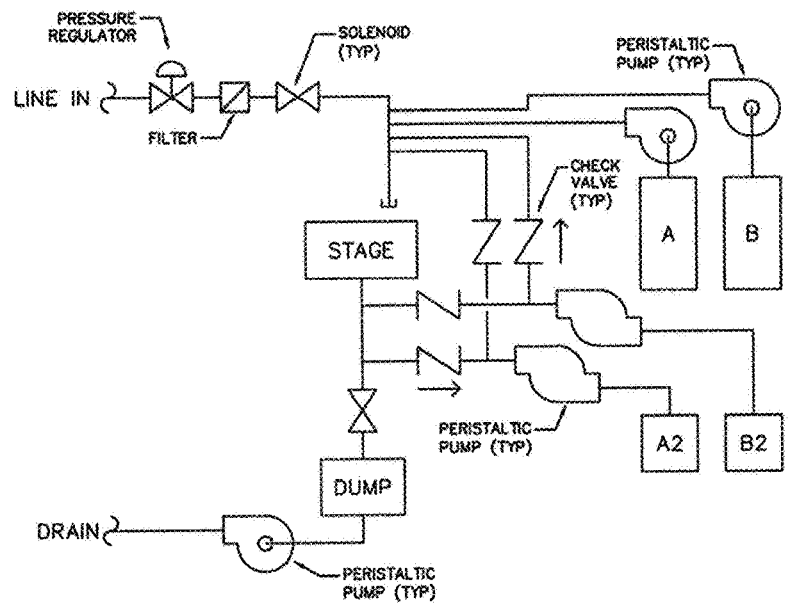
FIGS. 5A-C are schematic diagrams illustrating recycling of fluids into separate reservoirs, according to example embodiments.
Figure 5B:
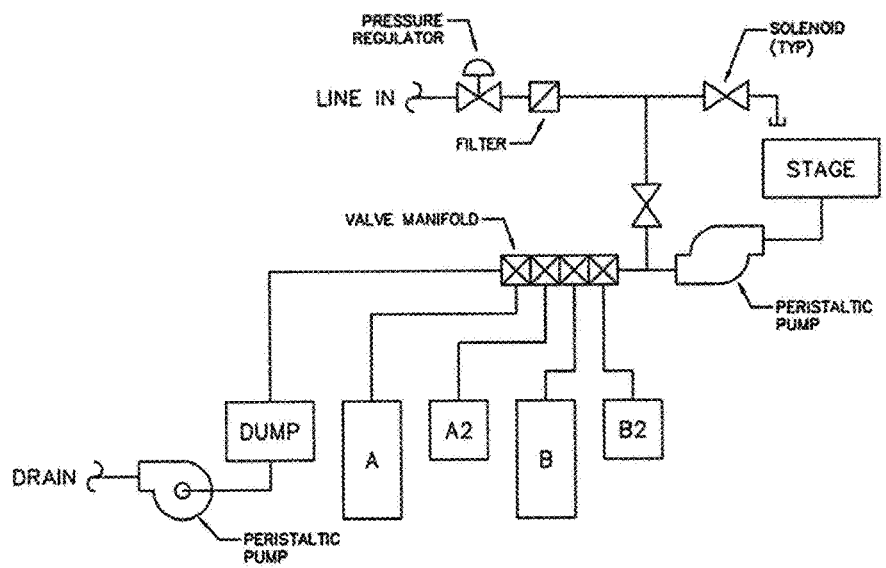
Figure 5C:
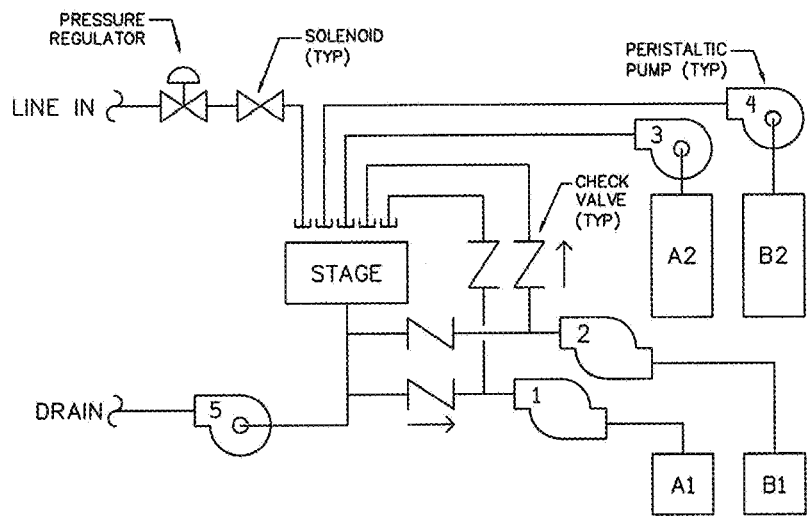

FIGS. 5A-C are plumbing schematics illustrating recycling of fluids into separate reservoirs. The example design shown in FIG. 5A includes multiple reversible pumps and check valves to control the flow from and back into the reservoirs. A second example design (not shown) can include syringe pumps to withdraw and store recycled fluids between cycles. A third example design, shown in FIG. 5B, includes a reversible pump and a solenoid valve manifold to direct fluid among multiple reservoirs.

Details of Particular Example Embodiment

A particular example embodiment, such as the system 100 illustrated in FIG. 1, of the disclosed systems can include a commercially-available 3D printer, (e.g., Printrbot Simple), augmented and modified for hydrogel extrusion and mineralization. The printer can be outfitted with a heated syringe paste extruder available from the manufacturer. The syringe can be modified, for example, with a 260 μm diameter needle for high-resolution extrusion. The needle can also be outfitted with additional hardware to facilitate heat transfer to keep the needle warm enough for hydrogel extrusion.

The example system can deliver two different solutions, as well as a water rinse, to the printed part. Additional reservoirs and pumps allow solution to be reused over multiple soak periods, reducing the need for large main solution supplies.

An aluminum plate with polycarbonate walls can be fastened onto the print stage and forms a chamber for both printing and soaking. Infrared sensors can monitor the fluid level in the chamber to prevent overflow. The stage and fluid lines can be made with hydrophobic materials to minimize residual solution remaining in the stage between cycles and causing undesired mineralization. Additionally, peristaltic pumps and pinch valves can be used throughout the system to minimize moving parts in direct contact with the salt solutions.

Fluid system controls can integrate directly with the extension pins on the printer's onboard circuit, for example. A custom software plugin may augment the standard set of g-code commands with custom commands for switching the fluid components. The printer's firmware may be modified, as known in the relevant art, to interpret these commands and toggle extension pins accordingly.

The device can be placed on a perforated aluminum platform, which allows fluid lines to be easily routed and organized underneath the printer. Such a raised platform also facilitates draining the stage and prevents the fluid components from interfering with the printer's motion.

Details of an Example 3D Printer

The 3D printer 105 of the example system 100 of FIG. 1 (e.g., Printrbot) has several desirable qualities: 50 μm positioning accuracy, reliability, a large user community, and open source software. It has a durable sheet-metal construction, a stage that moves in a single horizontal direction (X), and a print head that moves horizontally (Y) and vertically (Z). The manufacturer also offers a syringe pump extruder accessory. The 3D printer's 105 syringe extruder 110 includes a traditional plastic syringe with a Luer-lock head combined with a stepper motor, gear, and lead screw assembly that depresses the plunger. Although the unmodified syringe extruder 110 is intended for use with pastes, not hydrogels, the mechanisms required to print these materials are somewhat similar. Like gelatin, many pastes are highly viscous and must be heated before they can be extruded. The 3D printer's 105 paste extruder 110 contains a heating element capable of warming fluids up to 90° C., which can handle collagen's 40-60° C. melting point.

The paste extruder 110 head is designed with a 60 ml syringe contained in an aluminum body. The heat source is a cartridge heater inserted in the middle of the wall. The temperature can be set on Cura (an open-source 3D printing software program used by the 3D printer 105), which can read the temperature from a temperature probe that is placed in the containment vessel adjacent from the cartridge heater. Temperature control is important for gelatin extrusion because extruding the material requires it to be melted. Initial tests with gummy bears yielded an initial melting temperature of 65° C. Heating the syringe to 65° C. is well within the capabilities of the heater. However, in order to extrude the material with the desired accuracy of 260 μm, the gelatin can be extruded through a needle in the example embodiment. Based on the previously-described design of the stage and the geometry of the paste extruder 110, the needle should be slightly longer than an example wall height of one inch. As previously described, the melting temperature of the gelatin was determined to be 46.3° C. It is important that the temperature of the gelatin remain above 46.3° C. within the needle to avoid clogging. Initial tests with short needles, <1", directly attached to the syringe 110 resulted in clogging because the gelatin solidified in the needle body. Thus, the 3D printer extrusion component 110, as disclosed herein, can be modified to transferring heat to the needle.

Figure 6:
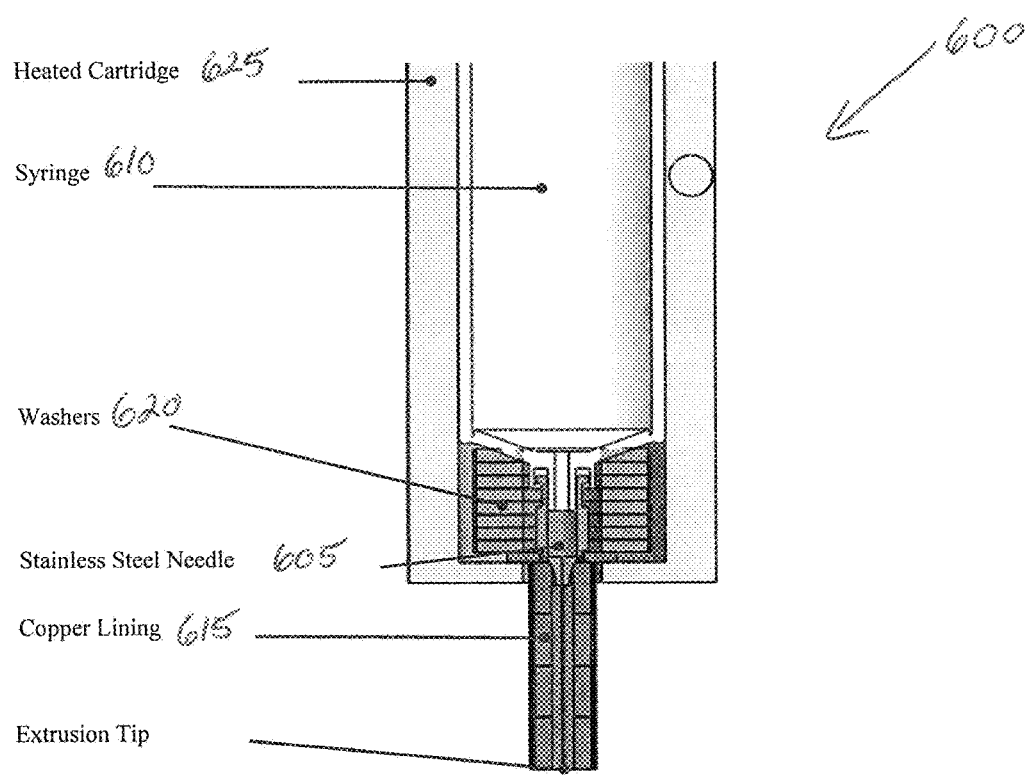
FIG. 6 is a schematic diagram illustrating a modified syringe extruder, according to an example embodiment.

With reference to FIG. 6, a needle 605 with an ID of 150 μm from McMaster-Carr, for example, can be used. The particular needle is 2" long, but can be shortened. The needle 605 is made entirely of 304 Stainless Steel, with a luer-lock fitting that fits with the syringe 610. To serve as insulation, a Teflon PTFE (Polytetrafleuoroethylene) tube with ¼" OD and ¹⁄₁₆" ID can be used. PTFE is a good insulator because it has very little thermal conductivity, 0.245 W/m-° C. A shim can be used to raise the body of the needle into the heated compartment 625. Then, a conductive metal washer 620 can be used to transfer heat directly from the aluminum body of the heater to the needle 605. The PTFE can serve as a sheath, insulating the needle 605 to maintain temperature. Initial simplified thermal FEA simulations in Fusion 360 suggest that the needle 605 can stay hot enough to extrude gelatin based on this design. A given configuration may be ineffective because there may not be sufficient material for transferring the heat to the needle. Thus, the needle 605 can be surrounded with a heated sleeve 615. Copper may be used for the heated sleeve 615, with thermal conductivity of 385 W/m° C. The needle 605 may be wrapped in copper foil tape with a conductive adhesive. The needle 605 of ID 260 μm can be placed in a sheath made of copper stand-offs that are also wrapped in copper tape. The standoffs may be attached to a stack of washers 620 held within the main body of the heated extruder 610. The washers 620 can be used to keep the main body of the needle 605 within the heated chamber of the extruder 600, as shown in FIG. 6. A special plunger head may also be used to allow air to be evacuated from the syringe 610 prior to insertion in the printer, which can increase the consistency of printer extrusion.

An FEA thermal analysis was conducted on copper standoffs wrapped in copper tape. Results show that with the main body 625 of the heater held at 60° C., the tip is expected to stay at 59.3° C. After installing a syringe extruder in place of the filament extruder, experiments with gelatin extrusion parameters were performed. The optimal extrusion temperature as a result of the experiments was 60 C, warm enough for gelatin to be melted at the tip of a 1.25" needle, but cool enough to avoid denaturing the gelatin contained within the heating chamber. A Cura profile was also generated that was well-suited for printing gelatin. The profile indicates what specific g-code commands Cura can write to generate the print. The parameters in the example Cura profile indicate the volumetric extrusion rate and the speed of the x, y, and z motors. Because the Cura user interface is intended for use with a filament extruder, g-code changes were determined that take place when each parameter is changed to predict how they will affect syringe extrusion. An example Cura profile that yielded positive results is illustrated in FIG. 7.

In some embodiments, a needle with an inner diameter of 0.012" (0.302 mm) was found to work well, with needles sizes between 0.008" and 0.05" being tested. A copper sheath may also be used to control the temperature of the needle, where the needle protrudes 5 mm out of the sheath. The sheath can be wrapped in an insulating material. In many embodiments, the needle is immersed in water (e.g., in a glass container) during mineralization phases. The water may be heated to keep the needle warm, for example, to about 5° C. warmer than the melting point of the particular polymer being printed. A heater pad may be used to warm the water in a glass container.

Details of an Example Fluid Delivery System

The example system 100 of FIG. 1 includes four reservoirs 130a, 130b, 145a, 145b, each with its own peristaltic pump 135a-d. Two of the reservoirs 130a, 130b (represented as A2 and B2 in FIG. 5C) are configured to contain fresh solution, and pumped in only one direction—to the stage 125—with no return using respective pumps (represented as 3 and 4 in FIG. 5C). The other reservoirs 145a, 145b (represented as A1 and B1 in FIG. 5C) are smaller and serve as holding vessels for recycled fluid. The pumps 135c, 135d for these reservoirs (represented as 1 and 2 in FIG. 5C) can be reversible, capable of both pumping fluid from the reservoir 145a, 145b to the stage 125 and vice-versa. The fluid can take a different path depending on the direction of pumping. To fill the stage 125, fluid can flow into the stage 125 from above. To drain the stage 125, fluid can be pulled from beneath the stage 125 back into the reservoir. Check valves may be used to control the path that the fluid takes.

Water entering the system 100 from an external source, such as a building hookup (line in), can pass through a pressure reducing valve, a filter, and a solenoid valve. The solenoid valve can open during the rinse cycle and remain closed otherwise. After each rinse cycle, a drain pump (represented as 5 in FIG. 5C) can run to drain the fluid from the system 100 into a separate fluid disposal container or directly to a drain. If a peristaltic pump is used, the pump can also act as a valve, eliminating any need for a separate drain valve and reservoir. The dump reservoir can, alternatively, be gravity-fed from the stage 125 and, once filled, the dump reservoir may be emptied using a pump.

Peristaltic pumps are well suited for the example system 100. They are capable of low flow rates, reversible flows, and keep the fluid separate from moving mechanical components. Peristaltic pumps that can be used in the example system are small, relatively cheap, and run on 12 VDC. They can use 2 mm ID, 4 mm OD flexible tubing and are capable of flow rates as high as 100 mL/min against a pressure head of one vertical meter. This information is sufficient for rough flow calculations to ensure the pumps would have sufficient power to operate within the system. A preliminary pressure loss calculation is presented in Appendix B. Tests demonstrate that such pumps are capable of consistently filling a 20 ml fluid volume in ~20 seconds, giving an observed flow rate of 1 ml/s. This flow rate would likely be accurate enough to simply command the pumps to fill for a given number of seconds; however to avoid potential issues, a level sensing system can be used in the soak area (chamber) 125 as well. A valve located beneath the stage can open to divert fluid in the stage to the drain. Because this valve is shared by all fluids, there is a greater risk of undesired mineralization. A pinch valve can mitigate this risk by isolating moving mechanical components from the fluid line. Such a valve can operate on 12 VDC and accept ⅛" ID, ¼" OD tubing.

Check valves can be used in the design of the example embodiment to control the path that the fluid takes depending on the direction in which a pump is operating. The check valves can be small, inexpensive, and easily connected to ⅛" ID hose via barbed connections. They may also be spring operated (e.g., minimum 1 psi opening pressure), which allows the valves to be mounted in any direction. The valves can have a polypropylene body, which, due to its hydrophobic nature (contact angle 102°), facilitates draining and rinsing, minimizing undesired mineralization.

The fluid for the rinse line can come from an external tap. In order for this to be integrated into the controlled fluid system, a regulator and a solenoid valve can be arranged between the external tap and the line going into the soaking area (chamber) 125. The regulator can include ¼" NPT ports and a manual knob for dialing the output pressure anywhere from 0-25 psi. By experimentally adjusting the output pressure, the flow rate from the regulator can be adjusted to be the same as from the peristaltic pumps. A 12 VDC solenoid valve can control the action of the rinse fluid. Crush-resistant silicone rubber tubing (PDMS) can be used throughout the fluids system 115. While the peristaltic pumps 135a-e can use 2 mm ID tubing, ⅛" tubing can be used elsewhere as fittings are more readily available in that size. This silicone tubing is very flexible, which facilitates installation. It also has excellent resistance to deionized water, and drains well due to its hydrophobicity (contact angle 107°). Barbed fittings may be used throughout the system, owing to their ease of assembly and compatibility with soft silicone tubing. All fittings may be made from chemical-resistant polypropylene, another hydrophobic polymer.

Details of an Example Stage Design

Figure 8:
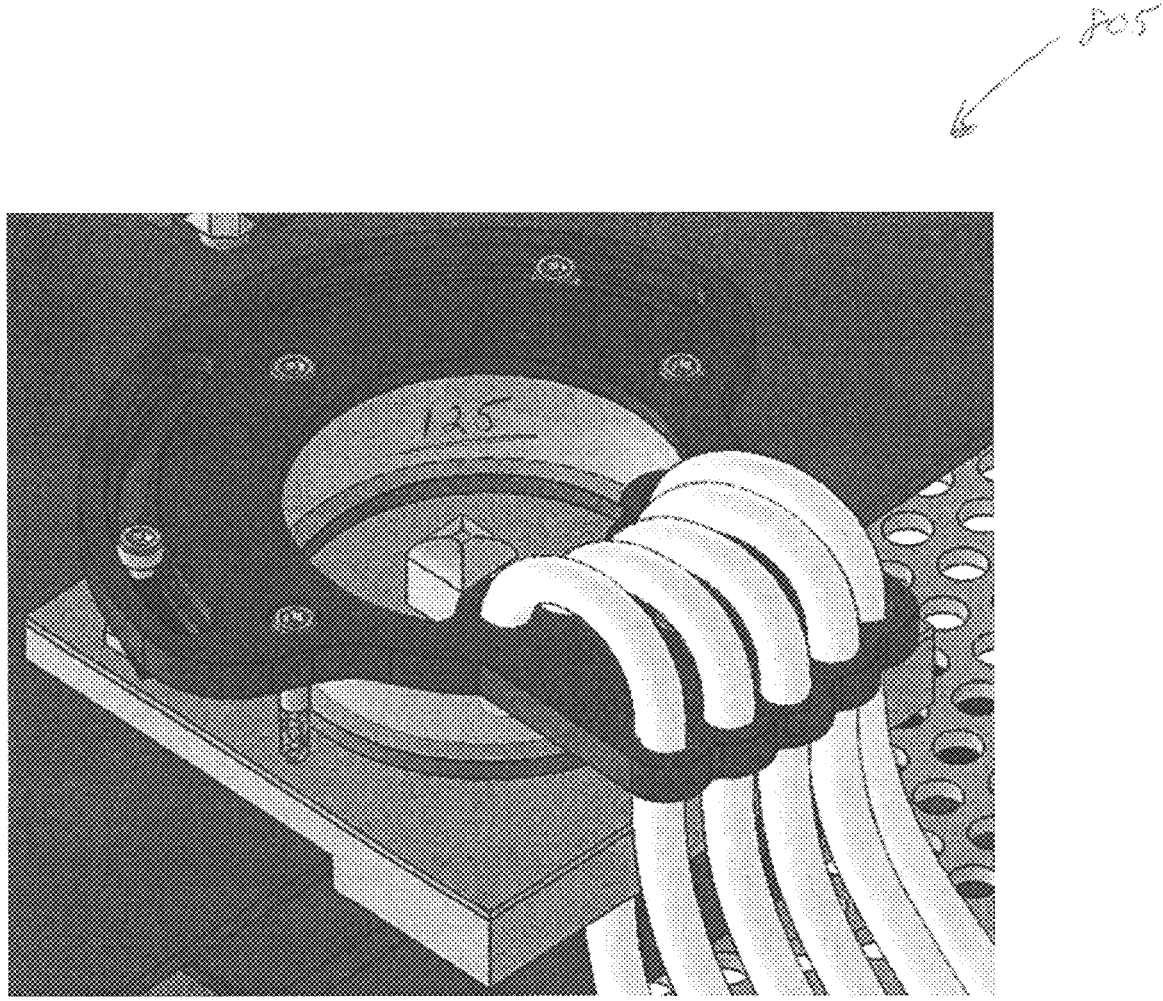
FIG. 8 is a schematic diagram illustrating an example design of a printing stage (chamber), according to an example embodiment.

The 3D printer stage 125 can be outfitted with custom hardware to meet the needs of both the printing and fluid treatment processes. The fluid system 115 of the example system 100 can use an enclosed volume with enough space for inflow and drain tubing. An example stage design 805 is illustrated in FIG. 8. The printer should have a planar surface on which to extrude material and enough clearance for the print head to move around the entire footprint of each printed layer. All components included in the stage design should be hydrophobic enough (contact angle greater than 90°) to avoid wetting and deposition of excess salts from the fluids. It would also be beneficial for the walls of the tank to be clear, to allow for continual visual inspection of the process. Thus, clear polyethylene may be used as a wall material. It has a contact angle of 96°, and is readily available in multiple shapes, allowing for easy manipulation of the wall geometry. The extruder needle 150 should be kept as short as possible to reduce the amount of heat lost to free convection. In order to accommodate this restriction, the total height of the walled chamber 125 may be set to one inch, for example. This height allows the needle tip to remain at a temperature high enough for extrusion and also leaves enough overhead room for the printed part to be totally submerged in fluid.

Regarding the floor of the stage 125, because the print head extrudes material onto the surface, there should be sufficient friction to allow the first layer to properly adhere. This means that surface wetting would be better, but that draining the stage would be more difficult. A relatively small stand-off platform may be used on the floor of the stage 125 to keep the printed layers above any standing liquid. Acrylic can be used as a material for the stage floor. To further improve the draining of the fluids, a chamfer may be added to the edge of the drain hole to allow the standing water droplets to fall over the edge more easily.

Details of Example Controls

Figure 9:
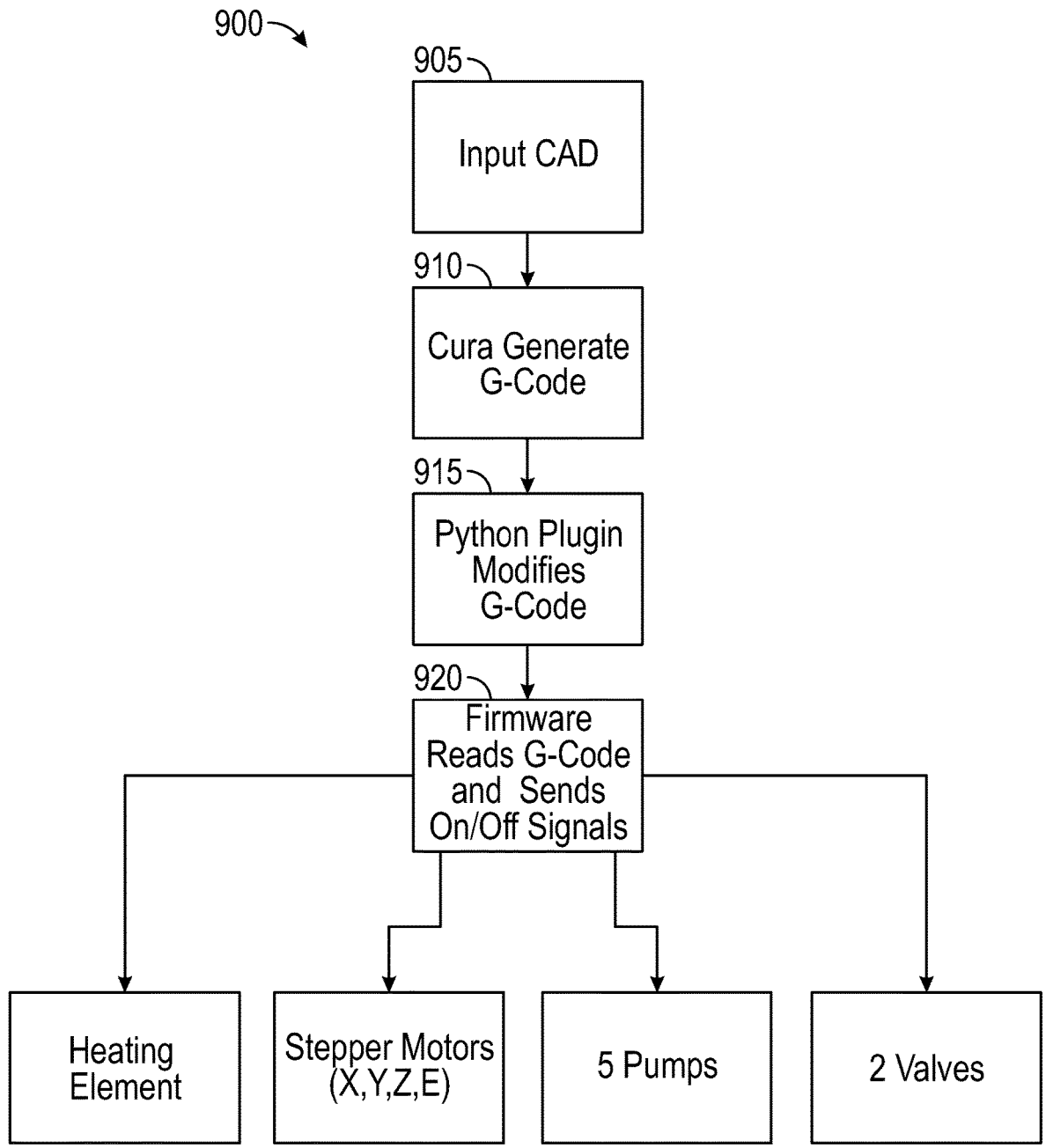
FIG. 9 is a flow diagram illustrating example control of a three-dimensional printing and mineralizing system, according to an example embodiment.

In the example system 100, a control unit 120 integrates the fluid delivery system 115 and 3D printing system 105, ensuring reliable, seamless, and autonomous execution of the printing and mineralization processes. The bridge between the 3D printer unit 105 and fluid delivery system 115 can involve three aspects: electronics, firmware, and a software plugin. FIG. 9 illustrates an example control scheme 900 on a high level. According to the example control scheme 900, a computer aided design (CAD) file may be taken as input 905. 3D printer software (e.g., Cura) can be used to generate 910 3D printing code (g-code) from the CAD design. A Python plugin can be used to modify 915 the generated 3D printing code. The system firmware can read the modified g-code and send 920 control signals to system components.

Example Electronics Design

Proper control of the pumps and valves of the fluid system 115 is an important aspect of the example system's functionality. An Arduino (an open-source electronics platform), for example, may be used to control these components. Alternatively, available extension pins that are part of an off-the-shelf 3D printer can be used instead of an Arduino.

Figure 10:
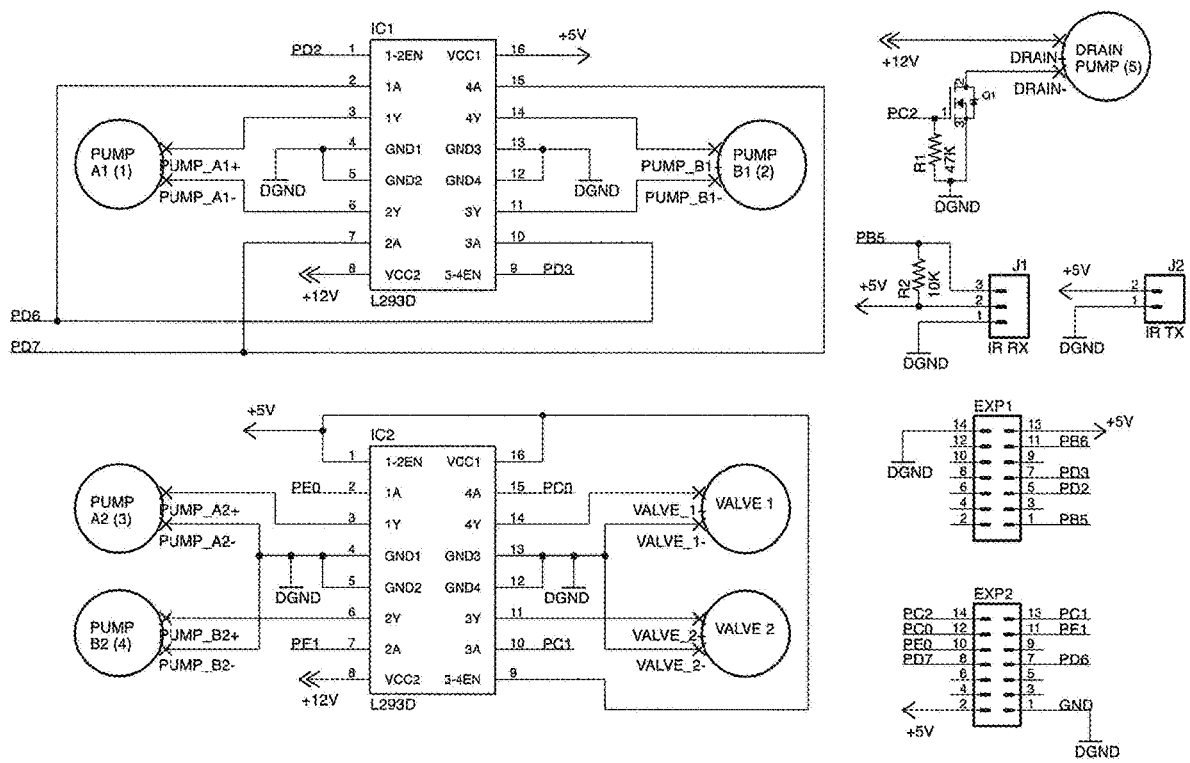
FIG. 10 is a diagram illustrating an example electrical schematic for components of a fluid delivery system, according to an example embodiment.

FIG. 10 illustrates an example electrical schematic for fluid system components. In the example embodiment, the peristaltic pumps and the solenoid valves are powered by 12 VDC and draw between 200-300 mA of current. The circuit logic operates at 5 VDC. These are the same levels used by the off-the-shelf Printrbot 3D printer, so the two systems can interconnect seamlessly. To switch the components at 12 VDC using 5 VDC logic, two dual H-bridges and a single N-channel MOSFET transistor can be used. The H-bridges are capable of controlling two bi-directional devices, which is important because the two pumps for the recycle reservoirs can be reversible in the example embodiment. Alternatively, these H-bridges can control up to four single-directional devices. A MOSFET may be used to control the remaining pump rather than adding another H-bridge.

The electrical layout can also incorporate a level sensor. Level sensing within the print and soak chamber 125 prevents overflow onto the stage 125 in the event of excess pump runtime or a clog in the drain. Multiple types of level sensing may be used (e.g., a float switch, an infrared distance sensor, and an infrared break-beam sensor). The example system 100 can use an infrared transmitter and receiver, mounted on diametric opposite sides of the print chamber. When the fluid level is low, the beam travels from the transmitter, through the chamber's clear acrylic walls, and is registered by the receiver. When the fluid level reaches sufficiently higher, it refracts the beam enough to prevent it from reaching the receiver, triggering the sensor. For a static, non-contact system, it is highly reliable and does not interfere with printing. The sensor can use 5V digital output that is easily read by the printer's microcontroller.

Example Firmware Modifications

A Printrbot 3D printer runs on Marlin firmware, a common open source, C++ based 3D printing firmware that is used on multiple platforms. Through modification of Marlin, custom G-code commands (see Appendix C) can be implemented to control extension pins of the Printrbot's circuit board, thereby controlling the fluid system. Code that reads and interprets the G-code is in a "Marlin_main.h" file, which is where most changes can be made.

In addition to defining new G-code commands, a custom function can be defined in Marlin_main.h that is executed in a loop while fluid system components are running and that constantly monitors the status of the level sensor. If the sensor is tripped, the function breaks the loop and shuts off components (e.g., pumps). The sensitivity and desired state of the sensor can be set with G-code. More detail is provided in Appendix C.

Firmware changes can also adjust the behavior of the printer 105 to account for the modified syringe extruder 110, 150. This may be accomplished by defining a new printer name, and associating that printer name with custom default parameters and setting appropriate temperature, speed, and position limits.

Example Cura Plugin

Cura is an open-source 3D printing software used by Printrbot and many other 3D printers. Before the 3D printer 105 can being extruding, an input CAD model must first be translated into language the printer can understand—a series of location commands called G-code. The process of generating G-code from CAD is called slicing. In addition to commanding locations, G-code also can also modify the printer's settings, such as temperature, speed, and limits, as known in the relevant art.

Cura allows users to install plugins, written in Python, that modify the G-code before it is sent to the printer, enabling a high level of control over the printer's behavior. A custom plugin that may be used in some embodiments can operate by reading the G-code generated by Cura, iterating through the code line-by-line, and adding/removing/modifying the code as necessary. The plugin's primary purpose can be to add the custom G-code commands to control the fluid system. Due to the cyclical, repetitive nature of the mineralization process, the software can be designed in a modular structure that limits the amount of redundant code. At intervals throughout the G-code, the plugin may call a function (e.g., "runFluids") that writes most of the custom G-code. The behavior of this function can vary depending on its input variables, allowing it to execute a priming sequence (e.g., rinses the fluid system and pre-fills reservoirs prior to printing), a post-print drain sequence (e.g., discards remaining fluid in the stage and recycle reservoirs and rinses the system), or a standard sequence. The plugin can also track how often to recycle fluids, how many cycles to execute, how long to run pumps, etc.

The plugin can also play a role in collision avoidance. Before every print, it may reload the printer's hardcoded default settings, which ensures all axis are properly oriented (e.g., Software +X direction is hardware +X, not −X). It may also divide particular X-Y-Z G-code commands into separate X-Y and Z commands so that the print head moves to the proper X-Y location before plunging, or so that the print head moves up before moving to the commanded X-Y location. Dividing the moves in this manner can avoid collision with the walls of the print and soak chamber 125. A user can modify the behavior of such a plugin by adjusting the parameters in Cura's "Plugins" tab. A detailed description of each parameter and its effect is listed in Appendix D.

Example Cura Profile

To tune the behavior of hydrogel extrusion, parameters may be available through the standard Cura interface. These parameters determine how Cura generates the G-code for a build; for example, Cura can change the federate in the G-code to match the travel speed specified by a user. The parameters displayed by Cura are intended for use with a filament extruder. Because the example embodiment includes a syringe extruder 110, 150, the parameters (e.g., flow percentage, filament diameter, layer height, and nozzle size) can be adjusted to achieve a high-quality print.

System Operation

Figure 11:
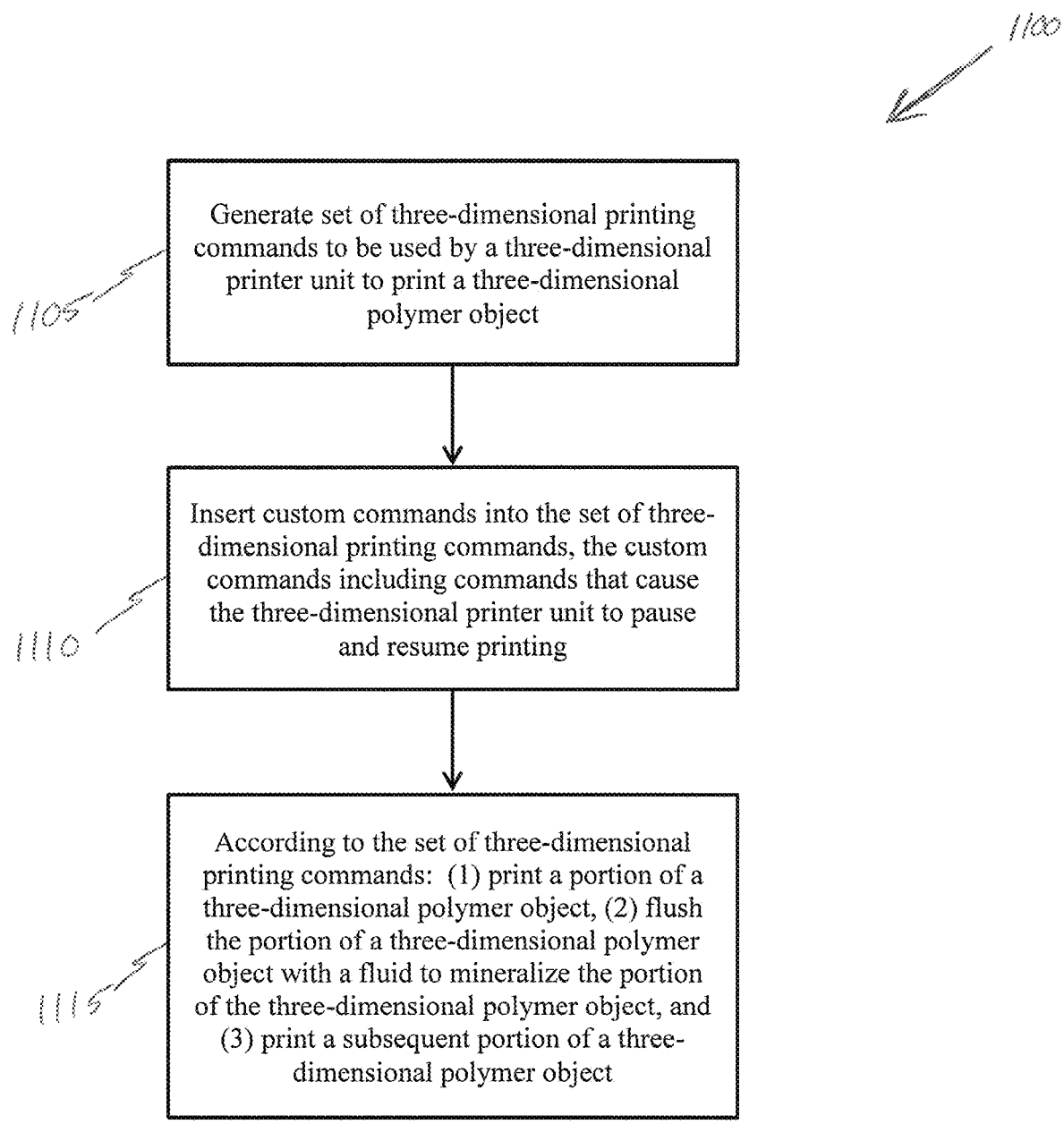
FIG. 11 is a flow diagram illustrating a method for printing and mineralizing a polymer, according to an example embodiment.

Integrated software controls can allow the three-dimensional mineralization printer to operate following a simple procedure. FIG. 11 is a flow diagram illustrating a method 1100 for printing and mineralizing a polymer, according to an example embodiment. The example method includes generating 1105 a set of three-dimensional printing commands to be used by a three-dimensional printer unit to print a three-dimensional polymer object, inserting 1110 custom commands into the set of three-dimensional printing commands, the custom commands including commands that cause the three-dimensional printer unit to pause and resume printing, and according to the set of three-dimensional printing commands with the custom commands 1115, (i) printing a portion of a three-dimensional polymer object, (ii) flushing the portion of the three-dimensional polymer object with a fluid to mineralize the portion of the three-dimensional polymer object, and (iii) printing a subsequent portion of the three-dimensional polymer object.

As a particular example of such a procedure, a user can upload an STL file to print into Cura. The user then loads the custom profile settings illustrated in FIG. 7 and a custom plugin. In the plugin interface, the user may define desired mineralization parameters. The user then loads the extruder 110, 150 with a custom syringe filled with polymer. The extruder's plunger may be lowered manually using Pronterface until extrusion begins. The user then waits until the extrusion slows down, meaning the pressure has been relieved. At this point, the system is ready to print. Once the plugin and profile are finalized and the STL file has been loaded, Cura can generate G-code to autonomously conduct the entire mineralized print.

Appendix A: Reservoir Volume Calculations

For a self-contained, non-diluting system, the volume of each fluid required can be given by the following formula:

$$V_{Res} = \left(\frac{N_{cycles}}{N_{recycle}}\right) V_{cycle} \tag{D1}$$

where $V_{Res}$ is the reservoir volume, $V_{cycle}$ is the volume of fluid required per cycle, $N_{recycle}$ is the number of cycles a solution is reused for, and $N_{cycles}$, the total number of cycles, is given by:

$$N_{cycles} = \left(\frac{H_{build}}{H_{layer}}\right) N_{layer} \tag{D2}$$

where $H_{build}$ is the height of the printed object, $H_{layer}$ is the height of a single printed layer, and $N_{layer}$ is the number of cycles per layer.

Assuming a build height of 8 mm, a layer resolution of 100 μm, a cycle volume of 20 mL, 10 fluid cycles per layer, and no recycling ($N_{recycle}=1$), the required reservoir volume would be 16 L. Under the same assumptions, but instead recycling every 10 cycles ($N_{recycle}=10$), the reservoir volume drops to 1.6 L.

Calculation of the required reservoir size for a diluting, non-recycling system can follow a similar method. The reservoir volume is the mass of water required to dilute all of the salt ($m_{H2O}$) divided by the density of water ($P_{H2O}$):

$$V_{Res} = \frac{m_{H2O}}{\rho_{H2O}} \tag{D3}$$

The required mass of water is a function of the mass of the salt ($m_{salt}$) and the solubility of that salt in water ($S_{salt}$, in g/100 g $H_2O$):

$$m_{H2O} = 100 \times \left(\frac{m_{salt}}{S_{salt}}\right) \tag{D4}$$

Lastly, the total mass of salt required is a function of the salt's molar mass ($\mathcal{M}$), the molarity of the diluted solution (M), the volume of the dilution dispensed per cycle ($V_{cycle}$), and the number of cycles ($N_{cycles}$, calculated with Eqn. D2):

$$m_{salt} = (\mathcal{M})(M)(V_{cycle})(N_{cycles}) \tag{D5}$$

The molar masses of calcium nitrate and potassium phosphate are 164.09 and 174.18 g/mol, respectively. The mineralization process calls for 0.25M solutions of each. The solubility of calcium nitrate in water is 121.2 g/100 g $H_2O$, and the solubility of potassium phosphate is 92.3 g/100 g $H_2O$. Using the same values for $V_{cycle}$ and $N_{cycles}$ as before, and assuming water's density to be 1000 g/L, a single print would require around 650 grams of each salt. This translates into reservoir sizes of 0.54 L for the calcium nitrate solution and 0.44 L for the potassium phosphate solution. Note that these volumes do not account for the additional volume incurred by dissolving each salt into water, but they still serve as adequate estimates.

Appendix B: Preliminary Pressure Calculations

A peristaltic pump can be capable of flow rates up to 100 mL/min and pumping up to 1 m elevation. This information can provide the basis for a rough pressure loss estimate.

The silicone tubing that may be used throughout the system can have an ⅛" inner diameter. For a 100 mL/min flow rate, this equates to a flow velocity of 0.2105 m/s and a Reynold's number ($Re_d$) of 750.9, within the laminar range. To find the friction factor ($f_{lam}$), the formula for laminar Poiseuille flow is invoked:

$$f_{lam} = \frac{64}{Re_d} \quad (E1)$$

From there, the resulting head loss ($h_f$) is calculated by:

$$h_f = f \frac{L}{d} \frac{V^2}{2g} \quad (E2)$$

where L is the pipe length, d is the pipe diameter, V is the flow velocity, and g is the acceleration of gravity. For a one-meter length of tube, the resulting frictional loss is 0.06 meters.

Certain check valves may have a flow coefficient ($C_V$) of 0.2 (GPM/psi). For a 100 mL/min flow rate, this equates to a 0.132 psi pressure drop, or a 0.093 m head loss.

Appendix C: Custom G-Code Commands

Setting a command time value to 0 will cause the component to run indefinitely, until stopped by a P0 command. This is useful for manual testing, but the plugin should not write time-indefinite commands for components that fill the stage (i.e., P1 F0, P2 F0, P3 S0, P4 S0, P7 S0). Doing so will ignore the level sensor and risk overflowing the stage.

P0—Turns all fluid system components off (sets pins low).

P1—Controls pump A1. For forward, use F#, with # in milliseconds. For reverse, use R#. Example: P1 R2000 will drive pump A1 in reverse for 2000 milliseconds.

P2—Controls pump B1. For forward, use F#, with # in milliseconds. For reverse, use R#.

P3—Controls pump A2. Use S#, with # in milliseconds. Example: P3 S5000 will drive pump A2 for 2000 milliseconds.

P4—Controls pump B2. Use S#, with # in milliseconds.

P5—Controls drain pump. Use S#, with # in milliseconds.

P6—Controls valve 1—drain valve, no longer in use.

P7—Controls valve 2—rinse water line in valve. Use S#, with # in milliseconds.

P8—Tells printer to wait until a specified pin (S) reaches a specified state (X). States are −1 (flip), 0 (low), and 1 (high). Can be used in conjunction with level sensors. Example: P8 S13 X0 will wait until pin 13 reaches logic low.

P9—Logs the status of specified pin (X) every (Y) milliseconds for (S) milliseconds. Valid X values are 13 (level sensor) and 14 (extension for additional sensor). Example: P9 X13 S10000 Y500 will display the status of pin 13 (level sensor) on the console, refreshing every 500 ms for 10 seconds.

P10—Sets the value of (S) level_tripper and (X) target pin state (0=low, 1=high). Level_tripper determines how many times the system must register the target state before pronouncing the sensor tripped. This is intended to avoid false positives, however in practice these are rare and a low value (2) typically will suffice. The custom plugin can enter this command each print. Pin state 0 (low) corresponds to a high fluid level (IR sensor beam broken). Example: P10 S2 X0 sets the desired level state to 0 (low, fluid level maximum) and tells the system to wait until the target state is read twice.

P11—Runs the custom manage_levelsense( ) firmware function in a loop for (S) milliseconds. Once the level sensor is tripped (based on P10 settings), a "Level Tripped!" message can be logged to the console. Example: P11 S10000 will watch the level sensor for 10 seconds and provide feedback once tripped.

P99—Use this command to display messages on the Pronterface console. Avoid special characters and many capital letters. When using this command in the plugin, include a dummy character (-) before the line break (\n) to avoid having the message cut off. Example: P99 Job Done— will display "Job Done" on the console.

Appendix D: Mineralizer Plugin Parameters

Enable Printing: If checked, the printer will extrude hydrogel according to the input CAD. If unchecked, the printer will not operate.

Enable Mineralization: If checked, the system will perform mineralization. If printing is enabled, a mineralization sequence will execute periodically according to other parameters. If printing is not enabled, the system will run through a single sequence.

Prime Fluids Before Print: If checked, the system will fill prime the fluid lines and recycle reservoirs with fluid. This happens before any printing or mineralization.

Purge Fluids After Print: If checked, at the end of printing/mineralization, the system will drain and rinse the lines and recycle reservoirs.

Mineralization Z increment (mm): The incremental height at which to perform mineralization. If 0.5 mm, for example, the mineralization sequence will execute at every 500 µm of printed height.

Cycles Before Fluid Refresh: Number of cycles to recycle solution for before discarding and drawing new solution from the main reservoirs.

Cycles Each Increment: Number of cycles to perform every Z increment. A single cycle consists of one soak in each salt solution.

Cycles at End-of-print: Number of additional cycles to perform once the structure is fully printed.

SOAK TIME (s): Amount of time to soak the printed part in each solution.

PUMPING: Main→Stage (s): Amount of time to run pumps to bring fluid from main reservoirs to the stage. If excessive, level sensor will trigger shutoff to prevent overflow.

PUMPING: Recycle→Stage (s): Amount of time to run pumps to bring fluid from the recycle reservoirs to the stage. If excessive, level sensor will trigger shutoff to prevent overflow.

PUMPING: Stage→Recycle (s): Amount of time to run pumps to bring fluid from the stage to the recycle reservoirs.

RINSE: Drain closed (s): Amount of time to flush in rinse water before the drain pump turns on. Increasing the time will allow the stage to fill up more and improve rinsing. If excessive, level sensor will trigger shutoff to prevent overflow.

RINSE: Drain open (s): Amount of time to flush in rinse water while draining to clean the drain line.

RINSE: Number of rinses: Number of times to repeat the rinsing process in between salt solution exposures. Increasing the number of rinses will help avoid mineralization on system components, but uses more water and takes more time.

DRAINING: Empty stage (s): Amount of time to run the drain pump to discard the fluid in the stage.

DRAINING: Empty recycle reservoirs (s): Amount of time to run pumps to discard leftover fluid in recycle reservoirs once the print is complete.

PRIME: Main reservoir lines (s): Amount of time to run pumps to prime the lines from the main reservoirs to the stage, from the stage to the recycle reservoirs, and to fill the reservoirs (this all happens at once). Increasing this time will mean the print starts with more fluid in the recycle reservoirs. Avoid initially filling these reservoirs more than halfway, or risk overflowing them.

PRIME: Recycle reservoir lines (s): Amount of time to run pumps to prime the lines from the recycle reservoirs to the stage.

PRIME: Clear drain line (s): At the end of the priming sequence, amount of time to run the drain pump to clear fluid from the drain line.

Pause before mineralizing (ms): If greater than 0 seconds, at every mineralization Z increment the printer will move away from the workspace and pause for the given duration. This will happen regardless of whether or not mineralization is enabled.

Extrude on pause (mm): When (if) the printer pauses upon reaching a Z increment, amount to depress the extrusion plunger. Extruding/retracting between layers may improve hydrogel flow.

Retract on pause (mm): When (if) the printer pauses upon reaching a Z increment, amount to retract the extrusion plunger. Will happen after first depressing the plunger (if extrusion amount >0).

Head park X (mm): X coordinate print head will rest at during pause.

Head park Y (mm): Y coordinate print head will rest at during pause.

Z soft limit (mm): Lower limit of the z-axis—adjust to set the start height of the print. Higher values correspond to the print head starting further down. Setting this value too high can cause the extruder to jam into the print stage, potentially damaging the extruder and/or z-axis hardware. The good practice is to manually determine this value using Pronterface before printing. The default z soft-limit value will prevent you from moving the extruder head far down enough. To adjust, first enter "M502" (reset limits) into the console, followed by "M211 Z200" (200 will set the soft limit far below the stage, so be careful) and then "G28 X0 Y0 Z0" (home all axis). Then use the Pronterface UI to position the print head above the stage and very carefully lower the Z-axis until the extruder is barely touching the stage. Enter "M114" into the console to output the current print head location. The Z value output will be the proper soft limit value. Enter "M502" and close out of Pronterface.

Note: When using the Mineralizer plugin, ensure that the custom start and end g-code fields in Cura are empty. If not, the printer may behave unexpectedly and get damaged.

While example embodiments have been particularly shown and described, it will be understood by those skilled in the art that various changes in form and details may be made therein without departing from the scope of the embodiments encompassed by the appended claims. For example, while one example application for the systems and methods disclosed herein is the printing and mineralization of collagen, embodiment may also be used to print and mineralize various other polymers, including, for example, gelatin, poly-vinyl alcohol, polyethylene (PE), polypropylene, acetal, acrylic, nylon (polyamides), polystyrene, poly-vinyl chloride (PVC), acrylonitrile butadiene styrene (ABS), and polycarbonate. Further, while some specific salt solutions have been disclosed above, other salt solutions may be used. For example, the cations for the first solution can include Ammonium $NH^{+4}$, Calcium $Ca^{2+}$, Iron $Fe^{2+}$ and $Fe^{3+}$, Magnesium $Mg^{2+}$, Potassium $K^+$, Pyridinium $C_5H_5NH^+$, Sodium $Na^+$, or Copper $Cu^{2+}$. The anions for the second solution can include, for example, Acetate $CH_3COO^-$, Carbonate $CO_2^{-3}$, Chloride $Cl^-$, Citrate $HOC(COO)(CH_2COO^-)_2$, Cyanide $C\equiv N^-$, Fluoride $F^-$, Nitrate $NO^{-3}$, Nitrite $NO^{-2}$, Oxide $O^{2-}$, Phosphate $PO_3^{-4}$, Sulfate $SO_2^{-4}$.

What is claimed is:

1. A system for three-dimensional printing and mineralizing a polymer, the system comprising:
   a three-dimensional printer unit with a syringe extruder;
   a fluid delivery system operatively coupled to the three-dimensional printer unit; and
   a control unit operatively coupled to the three-dimensional printer unit and fluid delivery system, the control unit configured to:
      cause the three-dimensional printer unit to print a portion of a three-dimensional polymer object;
      cause the fluid delivery system to flush the portion of the three-dimensional polymer object with a fluid to mineralize the portion of the three-dimensional polymer object; and
      cause the three-dimensional printer unit to print a subsequent portion of the three-dimensional polymer object.

2. A system as in claim 1 wherein the fluid delivery system includes:
   a chamber in which the three-dimensional polymer object is printed;
   at least one fluid reservoir; and
   at least pump in fluid communication with the chamber and the fluid reservoir to transfer fluid from the fluid reservoir to the chamber.

3. A system as in claim 2 wherein the chamber includes a fluid level sensor in communication with the control unit and configured to operate with the control unit to prevent over-filling of the chamber.

4. A system as in claim 2 wherein the chamber includes a drain to remove fluid from the chamber.

5. A system as in claim 4 wherein the fluid delivery system includes at least one recycling reservoir in fluid communication with the drain to receive fluid from the chamber for reuse.

6. A system as in claim 5 wherein the fluid delivery system includes:
   two main fluid reservoirs;
   two main pumps in communication with the control unit and in fluid communication with the chamber and the respective fluid reservoirs to transfer fluid from the fluid reservoirs to the chamber;
   two recycling reservoirs; and
   two recycling pumps in communication with the control unit and in fluid communication with the chamber and the respective recycling reservoirs to transfer fluid from the chamber to the recycling reservoirs and from the recycling reservoirs to the chamber.

7. A system as in claim 6 wherein:
   a first of the two main fluid reservoirs is configured to contain a first salt solution with a given cation;
   a second of the two main fluid reservoirs is configured to contain a second salt solution with a given anion;
   a first of the two recycling reservoirs is configured to contain at least a portion of the first salt solution after being used to flush at least a portion of a three-dimensional polymer object; and a second of the two recycling reservoirs is configured to contain at least a portion of the second salt solution after being used to flush at least a portion of a three-dimensional polymer object.

8. A system as in claim 1 wherein the syringe extruder includes an insulated extended copper-lined tip to maintain a heated polymer within a certain temperature range as the heated polymer passes through the extended tip.

9. A system as in claim 1 wherein the polymer extruded by the syringe extruder is charged.

10. A system as in claim 1 wherein the control unit is configured to respond to custom commands inserted into a set of three-dimensional printing commands used by the three-dimensional printer unit.

11. A system as in claim 10 wherein the custom commands include commands that cause the three-dimensional printer unit to pause and resume printing.

12. A method for three-dimensional printing and mineralizing a polymer, the method comprising:
printing a portion of a three-dimensional polymer object;
flushing the portion of the three-dimensional polymer object with a fluid to mineralize the portion of the three-dimensional polymer object; and
printing a subsequent portion of a three-dimensional polymer object.

13. A method as in claim 12 wherein flushing the portion of a three-dimensional polymer object with a fluid includes transferring the fluid to a chamber in which the three-dimensional polymer object is printed.

14. A method as in claim 13 further comprising draining fluid from the chamber after flushing the portion of a three-dimensional polymer object with the fluid.

15. A method as in claim 14 wherein draining fluid from the chamber includes transferring the fluid from the chamber to a recycling reservoir for reuse.

16. A method as in claim 12 wherein flushing the portion of a three-dimensional polymer object with fluid includes:
transferring a first fluid from a first main reservoir to a chamber in which the three-dimensional polymer object is printed;
transferring the first fluid from the chamber to a first recycling reservoir;
transferring a second fluid from a second main reservoir to the chamber; and
transferring the second fluid from the chamber to a second recycling reservoir.

17. A method as in claim 16 wherein the first fluid includes a salt solution with a given cation, and wherein the second fluid includes a salt solution with a given anion.

18. A method as in claim 12 further comprising maturing the three-dimensional polymer object by immersing the three-dimensional polymer object in a buffer solution.

19. A method for three-dimensional printing and mineralizing a polymer, the method comprising:
generating a set of three-dimensional printing commands to be used by a three-dimensional printer unit to print a three-dimensional polymer object;
inserting custom commands into the set of three-dimensional printing commands, the custom commands including commands that cause the three-dimensional printer unit to pause and resume printing; and
according to the set of three-dimensional printing commands with the custom commands:
printing a portion of a three-dimensional polymer object;
flushing the portion of the three-dimensional polymer object with a fluid to mineralize the portion of the three-dimensional polymer object; and
printing a subsequent portion of a three-dimensional polymer object.

20. A method as in claim 19 wherein the set of three-dimensional printing commands causes the three-dimensional printer unit to pause printing before flushing the portion of a three-dimensional polymer object with the fluid, and wherein the set of three-dimensional printing commands causes the three-dimensional printer unit to resume printing after flushing the portion of a three-dimensional polymer object with the fluid.

21. A method as in claim 19 wherein the set of three-dimensional printing commands causes activation and deactivation of pumps and valves to flush the portion of the three-dimensional polymer object with the fluid.

* * * * *